(12) United States Patent
Smaby et al.

(10) Patent No.: US 9,504,527 B2
(45) Date of Patent: Nov. 29, 2016

(54) INTER-OPERATIVE SWITCHING OF TOOLS IN A ROBOTIC SURGICAL SYSTEM

(71) Applicant: Intuitive Surgical Operations, Inc., Sunnyvale, CA (US)

(72) Inventors: Niels Smaby, Palo Alto, CA (US); Gregory Dachs, II, San Mateo, CA (US); Nicola Diolaiti, Menlo Park, CA (US); Pushkar Hingwe, Los Altos, CA (US); Thomas R. Nixon, San Jose, CA (US); Bruce M. Schena, Menlo Park, CA (US); Nitish Swarup, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 324 days.

(21) Appl. No.: 14/218,300

(22) Filed: Mar. 18, 2014

(65) Prior Publication Data

US 2014/0276950 A1    Sep. 18, 2014

Related U.S. Application Data

(60) Provisional application No. 61/793,227, filed on Mar. 15, 2013.

(51) Int. Cl.
*G06F 19/00* (2011.01)
*A61B 19/00* (2006.01)

(52) U.S. Cl.
CPC ........... *A61B 19/2203* (2013.01); *A61B 34/30* (2016.02); *A61B 34/37* (2016.02)

(58) Field of Classification Search
CPC combination set(s) only.
See application file for complete search history.

(56) References Cited

U.S. PATENT DOCUMENTS

| 4,604,787 | A | * | 8/1986 | Silvers, Jr. | B23Q 3/15526 29/26 A |
| 6,120,433 | A | * | 9/2000 | Mizuno | A61B 34/70 600/102 |
| 6,434,507 | B1 | * | 8/2002 | Clayton | A61B 17/32002 600/104 |
| 6,645,196 | B1 | * | 11/2003 | Nixon | B25J 9/1664 128/898 |
| 7,883,458 | B2 | * | 2/2011 | Hamel | A61B 17/32002 600/1 |
| 8,357,144 | B2 | * | 1/2013 | Whitman | A61B 10/0233 128/898 |

(Continued)

FOREIGN PATENT DOCUMENTS

EP           2138105 A2    12/2009
WO   WO-2010104753 A1     9/2010

OTHER PUBLICATIONS

Written Opinion for Application No. PCT/US2014/031044, mailed on Jul. 8, 2014, 5 pages.

(Continued)

*Primary Examiner* — Jonathan L Sample

(57) ABSTRACT

Methods, apparatus, and systems for controlling a telesurgical system are disclosed. In accordance with a method, a first tool connected to a first manipulator of the system, and a second tool connected to a second manipulator of the system, are controlled. A swap of the tools such that the first tool is connected to the second manipulator and the second tool is connected to the first manipulator is then detected. The first tool connected to the second manipulator and the second tool connected to the first manipulator are then controlled.

22 Claims, 25 Drawing Sheets

(56) References Cited

U.S. PATENT DOCUMENTS

| | | | | |
|---|---|---|---|---|
| 8,423,182 B2* | 4/2013 | Robinson | ............ | A61B 18/1206 |
| | | | | 700/245 |
| 8,672,837 B2* | 3/2014 | Roelle | ................ | A61B 1/00006 |
| | | | | 600/117 |
| 2002/0032452 A1* | 3/2002 | Tierney | .................. | G06Q 30/02 |
| | | | | 606/130 |
| 2006/0106493 A1* | 5/2006 | Niemeyer | ............... | A61B 34/70 |
| | | | | 700/245 |
| 2007/0299427 A1* | 12/2007 | Yeung | ...................... | B25J 9/047 |
| | | | | 606/1 |
| 2008/0046122 A1* | 2/2008 | Manzo | ............... | A61B 1/00149 |
| | | | | 700/245 |
| 2008/0200794 A1* | 8/2008 | Teichman | .............. | A61B 34/20 |
| | | | | 600/407 |
| 2009/0076476 A1* | 3/2009 | Barbagli | ................ | A61B 90/06 |
| | | | | 604/500 |
| 2009/0163929 A1* | 6/2009 | Yeung | ...................... | B25J 9/047 |
| | | | | 606/130 |
| 2010/0228264 A1* | 9/2010 | Robinson | ............ | A61B 18/1206 |
| | | | | 606/130 |
| 2010/0228588 A1* | 9/2010 | Nielsen | .................. | G06Q 10/06 |
| | | | | 705/7.11 |
| 2011/0082452 A1* | 4/2011 | Melsky | .................. | A61B 18/24 |
| | | | | 606/15 |
| 2011/0295248 A1* | 12/2011 | Wallace | ................ | B25J 9/1689 |
| | | | | 606/33 |
| 2011/0319714 A1* | 12/2011 | Roelle | ................ | A61B 1/00006 |
| | | | | 600/118 |
| 2011/0319815 A1* | 12/2011 | Roelle | ................ | A61B 1/00149 |
| | | | | 604/95.01 |

OTHER PUBLICATIONS

International Search Report for Application No. PCT/US2014/031044, mailed on Jul. 8, 2014, 4 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

INTER-OPERATIVE SWITCHING OF TOOLS IN A ROBOTIC SURGICAL SYSTEM

CROSS-REFERENCES TO RELATED APPLICATIONS

The present application claims the benefit under 35 USC 119(e) of U.S. Provisional Application No. 61/793,227 filed Mar. 15, 2013. The full disclosure of which is incorporated herein by reference in its entirety for all purposes.

The present application is generally related to the following commonly-owned applications: U.S. Provisional Application No. 61/683,495, filed Aug. 15, 2012, entitled "Phantom Degrees of Freedom for Manipulating the Movement of Robotic Systems", U.S. Provisional Application No. 61/654,764 filed Jun. 1, 2012, entitled "Commanded Reconfiguration of a Surgical Manipulator Using the Null Space", U.S. application Ser. No. 12/494,695 filed Jun. 30, 2009 (Allowed), entitled "Control of Medical Robotic System Manipulator About Kinematic Singularities;" U.S. application Ser. No. 12/406,004 filed Mar. 17, 2009 (now U.S. Pat. No. 8,271,130), entitled "Master Controller Having Redundant Degrees of Freedom and Added Forces to Create Internal Motion;" U.S. application Ser. No. 11/133,423 filed May 19, 2005 (now U.S. Pat. No. 8,004,229), entitled "Software Center and Highly Configurable Robotic Systems for Surgery and Other Uses;" U.S. application Ser. No. 10/957,077 filed Sep. 30, 2004 (now U.S. Pat. No. 7,594,912), entitled "Offset Remote Center Manipulator For Robotic Surgery;" and U.S. application Ser. No. 09/398,507 filed Sep. 17, 1999 (now U.S. Pat. No. 6,714,839), entitled "Master Having Redundant Degrees of Freedom," the disclosures of which are incorporated herein by reference in their entireties.

BACKGROUND

The present invention generally provides improved surgical and/or robotic devices, systems, and methods.

Minimally invasive medical techniques are aimed at reducing the amount of extraneous tissue which is damaged during diagnostic or surgical procedures, thereby reducing patient recovery time, discomfort, and deleterious side effects. Millions of surgeries are performed each year in the United States. Many of these surgeries can potentially be performed in a minimally invasive manner. However, only a relatively small number of surgeries currently use these techniques due to limitations in minimally invasive surgical instruments and techniques and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, such apertures resulting in the trauma typically associated with open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Provisional Application No. 61/654,764 filed Jun. 1, 2012, entitled "Commanded Reconfiguration of a Surgical Manipulator Using the Null Space", and U.S. Pat. Nos. 6,758,843; 6,246,200; and 5,800,423, the full disclosures of which are incorporated herein by reference in their entirety. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing dangerous forces against the abdominal wall. Alternative manipulator structures are described, for example, in U.S. Pat. Nos. 7,594,912, 6,702,805; 6,676,669; 5,855,583; 5,808,665; 5,445,166; and 5,184,601, the full disclosures of which are incorporated herein by reference in their entirety.

While the new robotic surgical systems and devices have proven highly effective and advantageous, still further improvements would be desirable. In some cases, it is desirable to change portions or all of manipulator assemblies, where a manipulator assembly may include a tool (e.g., a surgical tool) connected to a manipulator (e.g., robotic arm). For example, it may be desirable to change a robotic arm from a parallelogram arrangement that structurally constrains movement about a remote center to an alternative manipulator structure that uses, e.g., software control to constrain movement about the remote center. For another example, it may be desirable to change a tool connected to a manipulator from, e.g., one with clamping jaws to one with an endoscope.

In any event, a different manipulator assembly will often have different characteristics, such as a different number of degrees of freedom, different types of degrees of freedom, etc. Accordingly, the same controller for controlling the different manipulator assemblies cannot be used, but rather a different controller that performs, e.g., calculations in joint space, must be used that is customized to each specific tool and/or manipulator. The use of different controllers results in added layers of complexity that make the system more prone to error, and may effectively limit the use of new manipulators and/or tools with a preexisting system. While some techniques for providing system compatibility with new tools have been disclosed, such as those discussed in U.S. application Ser. No. 12/114,082 filed May 2, 2008 (U.S. Pat. No. 7,983,793), entitled "Tool Memory-Based Software Upgrades for Robotic Surgery," the disclosure of which is incorporated herein by reference in its entirety, further improvements are still desired.

For these and other reasons, it would be advantageous to provide improved devices, systems, and methods for surgery, robotic surgery, and other robotic applications. It would be particularly beneficial if these improved technologies provided the ability to conveniently switch between different types of manipulators and/or tools in an error-free fashion while keeping system complexity and costs low.

BRIEF SUMMARY

The present invention generally provides improved robotic and/or surgical devices, systems, and methods. In one embodiment, a method for controlling a telesurgical system is disclosed. The method includes various operations, including controlling a first tool connected to a first manipulator of the system, and a second tool connected to a second manipulator of the system. The method further includes detecting a swap of the tools such that the first tool is connected to the second manipulator and the second tool is connected to the first manipulator. The method also includes controlling the first tool connected to the second manipulator and the second tool connected to the first manipulator.

In accordance with another embodiment, another method for controlling a telesurgical system is disclosed. The method includes various operations, including determining whether a tool is connected to a manipulator of the system, acquiring a mapping for the tool when it is determined that the tool is connected to the manipulator, controlling the tool using the acquired mapping, determining whether the tool is removed from the manipulator and a new tool is connected to the manipulator, acquiring a new mapping for the new tool when it is determined that the tool is removed from the manipulator and a new tool is connected to the manipulator; and controlling the new tool using the acquired new mapping.

In accordance with yet another embodiment, a telesurgical system for performing minimally invasive surgery through an aperture of a patient is disclosed. The system includes a plurality of robotic manipulators each operable to receive one of a plurality of tools including an imaging device and a surgical instrument, and a controller. The controller may be operable to perform a variety of functions. For example, the controller may control an imaging device connected to a first manipulator of the robotic manipulators and a surgical instrument connected to a second manipulator of the robotic manipulators, detect a swap of the imaging device and the surgical instrument such that the imaging device is connected to the second manipulator and the surgical instrument is connected to the first manipulator, and control the imaging device connected to the second manipulator and the surgical instrument connected to the first manipulator.

For a fuller understanding of the nature and advantages of the present invention, reference should be made to the ensuing detailed description and accompanying drawings.

Other aspects, objects and advantages of the invention will be apparent from the drawings and detailed description that follows.

BRIEF DESCRIPTION OF THE DRAWINGS

FIG. 12A shows a connector/joint space map according to an embodiment.

FIG. 12B shows a joint space/work space map according to an embodiment.

DETAILED DESCRIPTION

Figure 1A:
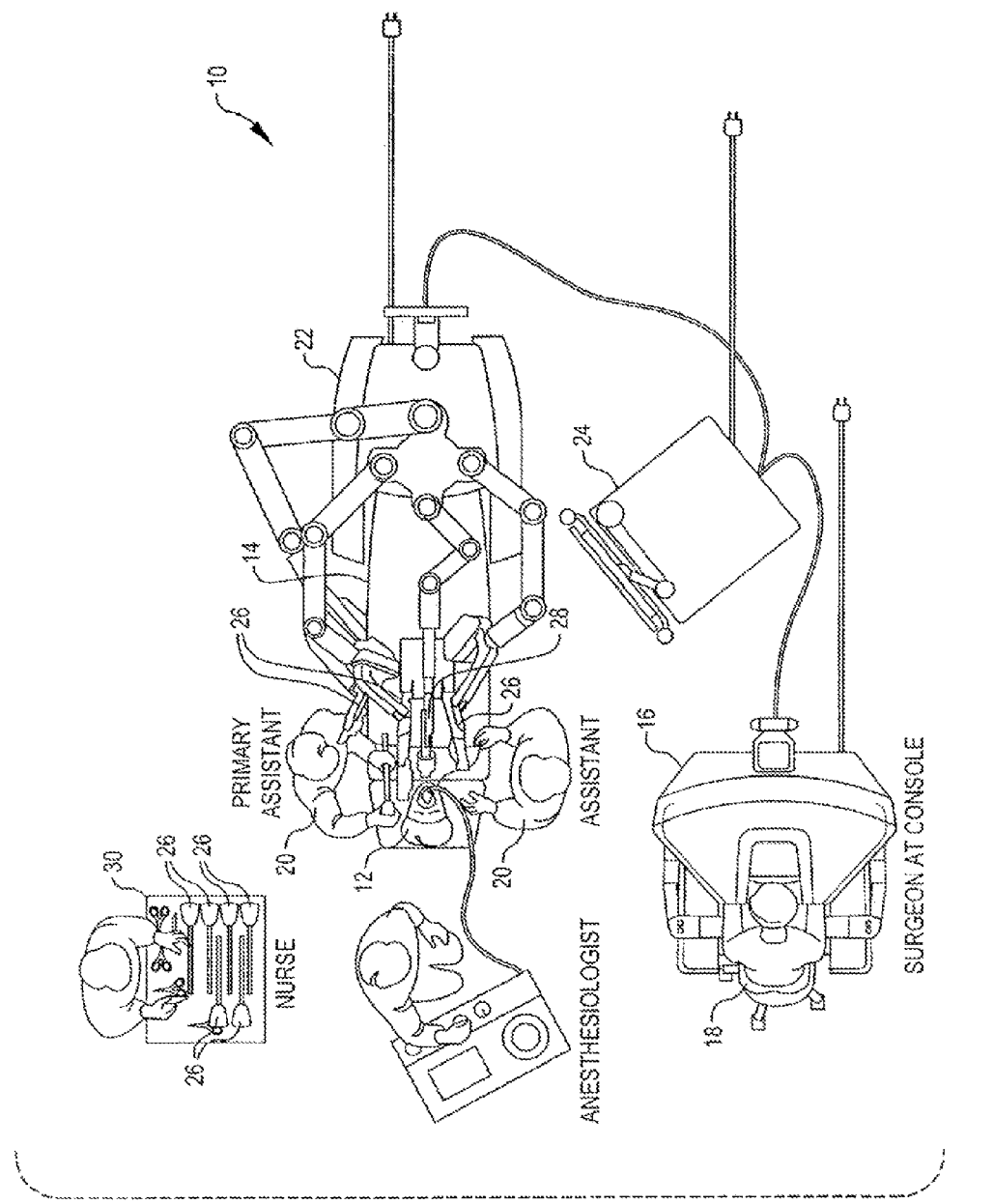
FIG. 1A is an overhead view of a robotic surgical system in accordance with embodiments of the present invention.

Embodiments of the present invention generally provide improved techniques for controlling a number of different manipulator assemblies. Some embodiments are particularly advantageous for use with surgical robotic systems in which a plurality of surgical tools or instruments are mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to control a number of different manipulator assemblies, such as different robotic arms and/or surgical tools, the flexibility of the robotic systems in performing surgical procedures may be significantly increased.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector which is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. For example, the manipulator assembly may include kinematic degrees of freedom of a manipulator as well as kinematic degrees of freedom of a tool connected to the manipulator. The combination of these may be referred to herein as "manipulator degrees of freedom", and are typically defined in joint space. Actuation of the end effector (such as opening or closing of the jaws of a gripping device, energizing an electrosurgical paddle, activating air pressure for a vacuum, or the like) will often be separate from, and in addition to, these manipulator assembly degrees of freedom. These may be referred to herein as "actuation degrees of freedom".

The end effector (or, more generally, the control frame, as described below) will typically move in the work space with between two and six degrees of freedom, but may move in work spaces with fewer than two or greater than six degrees of freedom. The degrees of freedom of the end effector (or, more generally, the degrees of freedom of the control frame) may be referred to herein as "end effector degrees of freedom", and are typically defined in a Cartesian work space (described below). As used herein, the term "position" encompasses both location (e.g., x, y, z coordinates) and orientation (e.g., pitch, yaw, roll). Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by one or more processors of the system so that a shaft or intermediate portion of the tool or instrument is constrained to a safe motion through a minimally invasive surgical access site or other aperture. Such motion may include, for example, axial insertion of the shaft through the aperture site into a surgical work space, rotation of the shaft about its axis, and pivotal motion of the shaft about a pivot point at the aperture site.

In one particular embodiment, kinematic degrees of freedom of a manipulator assembly may be controlled by driving one or more joints via the controller using motors of the system, the joints being driven according to coordinated joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator assembly has degrees of freedom, and in some exemplary embodiments, the joint space may have more dimensions than the manipulator assembly has degrees of freedom as the manipulator assembly may lack at least one degree of freedom necessary to fully define the position of an end effector associated with the manipulator assembly. Further, a particular configuration of the manipulator assembly may represent a particular point in the joint space, with each coordinate corresponding to a joint state of an associated joint of the manipulator assembly where an associated joint of the manipulator exists.

In an exemplary embodiment, the system includes a controller in which a commanded position and velocity of a feature in the work space, denoted here as its Cartesian space, are inputs. The feature may be any feature on the manipulator assembly or off the manipulator assembly which can be used as a control frame to be articulated using control inputs. An example of a feature on the manipulator assembly, used in many examples described herein, would be the tool-tip. Another example of a feature on the manipulator assembly would be a physical feature which is not on the tool-tip, but is a part of the manipulator assembly, such as a pin or a painted pattern. An example of a feature of the manipulator assembly would be a reference point in empty space which is exactly a certain distance and angle away from the tool-tip. Another example of a feature off the manipulator assembly would be a target tissue whose position relative to the manipulator assembly can be established. In all of these cases, the end effector is associated with an imaginary control frame which is to be articulated using control inputs. However, in the following, the "end effector" and the "tool tip" are used synonymously. Although generally there is no closed form relationship which maps a desired Cartesian space end effector position to an equivalent joint space position, there is generally a closed form relationship between the Cartesian space end effector and joint space velocities. The kinematic Jacobian is the matrix of partial derivatives of Cartesian space position elements of the end effector with respect to joint space position elements. In this way, the kinematic Jacobian captures the kinematic relationship between the end effector and the joints of the manipulator assembly. In other words, the kinematic Jacobian captures the effect of joint motion on the end effector.

Many (but not all) of the manipulator assemblies described herein have fewer degrees of freedom available for use than those that are typically associated with full control over the positioning of an end effector in a work space (where full control of the end effector requires end effector degrees of freedom including three independent translations and three independent orientations). That is, the manipulator assemblies may have an insufficient number or type of degrees of freedom for independently controlling the six end effector degrees of freedom. For example, a rigid endoscope tip without an articulating wrist may be missing two degrees of freedom at the wrist. Accordingly, the endoscope may have only four degrees of freedom for positioning the end effector, rather than six, thus potentially constraining the motion of the endoscope.

However, some of the manipulator assemblies described herein have a greater number of degrees of freedom than that required to fully control the positioning of the end effector (where full control of the end effector requires end effector degrees of freedom including three independent translations and three independent orientations), but due to the type or arrangement of the joints of the manipulator assemblies, the manipulator assemblies still cannot fully control the positioning of the end effector. For example, a manipulator assembly may have seven manipulator degrees of freedom, but three of those are redundant. As a result, the end effector effectively has five degrees of freedom. In some embodiments, the manipulator assemblies may have sufficient degrees of freedom to fully control the positioning of an end effector.

Regardless of the number of degrees of freedom available for controlling the position of the end effector, the manipulator assemblies described herein may also facilitate additional degrees of freedom for actuating a tool (i.e., actuation degrees of freedom). For example, the manipulator assemblies may be configured to mount a tool having an electro-cautery probe operable to, e.g., heat select tissue upon activation, where activation/deactivation of heat is a degree of freedom. For another example, the manipulator assemblies may be configured to mount a tool having a vacuum operable to, e.g., apply suction forces around select tissue upon activation, where actuating the suction forces is a degree of freedom. For yet another example, the manipulator assemblies may be configured to mount a tool having a grip, where actuation of the grip is a degree of freedom. For even yet another example, the manipulator assemblies may be configured to mount a tool having a grip and a cutter, where actuation of the grip is a degree of freedom and actuation of the cutter is a degree of freedom. In such cases, these additional degrees of freedom are not kinematic as they do not affect the position (i.e., location and orientation) of the end effector. Accordingly, these additional degrees of freedom may be referred to as 'non-kinematic' or 'actuation' degrees of freedom. This is in contrast to kinematic degrees of freedom (e.g., the manipulator degrees of freedom described herein), as kinematic degrees of freedom impact the position of the end effector.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control systems that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In many embodiments, the tool of an exemplary manipulator arm pivots about a pivot point adjacent a minimally invasive aperture. In some embodiments, the system may utilize a hardware remote center, such as the remote center kinematics described in U.S. Pat. No. 6,786,896, the entire contents of which are incorporated herein in its entirety. Such systems may utilize a double parallelogram linkage which constrains the movement of the linkages such that the shaft of the instrument supported by the manipulator pivots about a remote center point. Alternative mechanically constrained remote center linkage systems are known and/or may be developed in the future. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a desired pivot point, as opposed to a mechanical constraint. By having the capability to compute software pivot points, different modes characterized by the compliance or stiffness of the system can be selectively implemented. More particularly, different system modes over a range of pivot points/centers (e.g., moveable pivot points, whereby the software defined pivot point may be moved from one location to another; passive pivot points, whereby a patient's body wall is relied on to enforce the constraint of going through the 'center'; fixed/rigid pivot point; soft pivot points; etc.) can be implemented as desired.

In many configurations, robotic surgical systems may include master controller(s) having a number of degrees of freedom fewer than, more than, or equal to the number of degrees of freedom which the remotely controlled robotic manipulator arms and/or tools have. In such cases, Jacobian based or other controllers used to control the robotic manipulator arms and/or tools typically provide complete mathematical solutions and satisfactory control. For example, fully controlling the position (i.e., location and orientation) of a rigid body can employ six independently controllable degrees of freedom of the rigid body, which includes three degrees of freedom for translations and three degrees of freedom for rotations. This lends itself nicely to a Jacobian based control algorithm in which a 6×N Jacobian matrix is used.

Although manipulator assemblies having a variety of degrees of freedom are disclosed herein, including assemblies having fewer than, the same number as, or more than the six degrees of freedom for fully controlling the position of an end effector, many embodiments of these assemblies lack at least one degree of freedom for fully controlling the position of the end effector. While the manipulator assemblies may lack one of these degrees of freedom, the input device controlling the manipulator assembly (e.g., a master control input device) may include the lacking degree of freedom. In accordance with embodiments of the present invention, in response to an input controlling the degree(s) of freedom missing at the manipulator assembly, the other degrees of freedom available at the manipulator assembly may provide motions so as to simulate control of the missing degree(s) of freedom. This may be done by using a kinematic model of the manipulator assembly that includes and performs calculations for the missing manipulator degree(s) of freedom. By performing such calculations, the remaining degrees of freedom of the manipulator assembly may be more effectively controlled to cause an end effector to appear to move along the requested degree(s) of freedom. Further, the use of such a kinematic model may advantageously reduce the complexity of facilitating the positioning and/or actuation of tools having different numbers of degrees of freedom.

In at least one embodiment, different manipulator assemblies may be configured to connect to the same base or support structure of the robotic surgery system. For example, different robotic arms may be configured to connect to the same support structure, and/or different surgical tools may be configured to connect to the same robotic arm. In some cases, the same connector element on different robotic arms may control different aspects of the robotic arms. For example, an uppermost connector element on one robotic arm may control a yaw of the robotic arm, whereas the uppermost connector element on another robotic arm may control a roll of the robotic arm.

To facilitate proper interpretation of signals being received by a controller in the support structure from the robotic arms, the mapping unit may be provided to map the signals received from the robotic arms to particular inputs of a controller such as a joint space controller. For example, a common joint space controller that may be used for a number of different manipulator assemblies may have a fixed set of input elements. The mapping unit for a particular robotic arm may then map the signals received from the robotic arm to the appropriate input elements of the joint space controller. For example, the mapping unit may map a signal received from the 'roll' connector element of the robotic arm to the a generic input element of the joint space controller. For a different robotic arm, the mapping unit may map a signal received from the 'roll' connector element of the robotic arm (which may be a different connector element than for the first robotic arm) to the same generic input element of the joint space controller. In such a fashion, the same joint space controller may be used to perform joint space calculations for a number of different manipulator assemblies.

Similarly, manipulator assembly specific mappings may be used to map signals between controllers that perform calculations in different types of spaces. For example, the support structure may, in addition to the joint space controller, include a work space controller such as a cart space controller that is operable to perform calculations in a, e.g., three dimensional work space. A mapping unit may thus be provided to map signals output from the joint space controller to input elements of the work space controller.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a patient 12 who is lying down on an operating table 14. The system can include a surgeon's console 16 for use by a surgeon 18 during the procedure. One or more assistants 20 may also participate in the procedure. The MIRS system 10 can further include a patient side cart 22 (surgical robot) and an electronics cart 24. The patient side cart 22 may include a number of robotic arms that can each manipulate at least one removably coupled tool assembly 26 (hereinafter simply referred to as a "tool") through a minimally invasive incision in the body of the patient 12 while the surgeon 18 views the surgical site through the console 16. An image of the surgical site can be obtained by an imaging device 28, such as a stereoscopic endoscope, which can be manipulated by the patient side cart 22 so as to orient the imaging device 28. The electronics cart 24 can be used to process the images of the surgical site for subsequent display to the surgeon 18 through the surgeon's console 16. The number of surgical tools 26 used at one time will generally depend on the diagnostic or surgical procedure and the space constraints within the operating room among other factors. If it is necessary to change one or more of the tools 26 being used during a procedure, an assistant 20 may remove the tool 26 from the patient side cart 22, and replace it with another tool 26 from a tray 30 in the operating room. Further, the specific robotic arms attached to the patient side cart 22 may also depend on the diagnostic or surgical procedure, and like the tools 26 can also be changed before, during, or after a procedure.

MIRS system 10 in certain embodiments is a system for performing a minimally invasive diagnostic or surgical procedure on a patient including various components such as a surgeon's console 16, an electronics cart 24, and a patient side cart 22. However, it will be appreciated by those of ordinary skill in the art that the system could operate equally well by having fewer or a greater number of components than are illustrated in FIG. 1A. Further, computational operations or functions described herein as being performed by one particular element of MIRS system 10 can be performed by other elements of MIRS system 10 or, in some embodiments, distributed to two or more elements of MIRS system 10. For example, functions described herein as being performed by electronics cart 24 may, in some embodiments, be performed by console 16 and/or patient side cart 22. Further, it should be recognized that multiple elements providing the same or similar functionality may also be implemented within MIRS system 10. For example, MIRS system 10 may include two or more consoles 16 that independently or in combination control/interact with one, two, or more patient side carts 22. Similarly, more than one electronics cart 24 may be provided (e.g., one for each console 16), or, in some embodiments, no cart 24 may be provided whereby the functionality described herein associated with cart 24 may be distributed to one or more consoles 16, carts 22, and/or other elements of MIRS system 10. Thus, the depiction of the system 10 in FIG. 1A should be taken as being illustrative in nature, and not limiting to the scope of the disclosure.

Figure 1B:
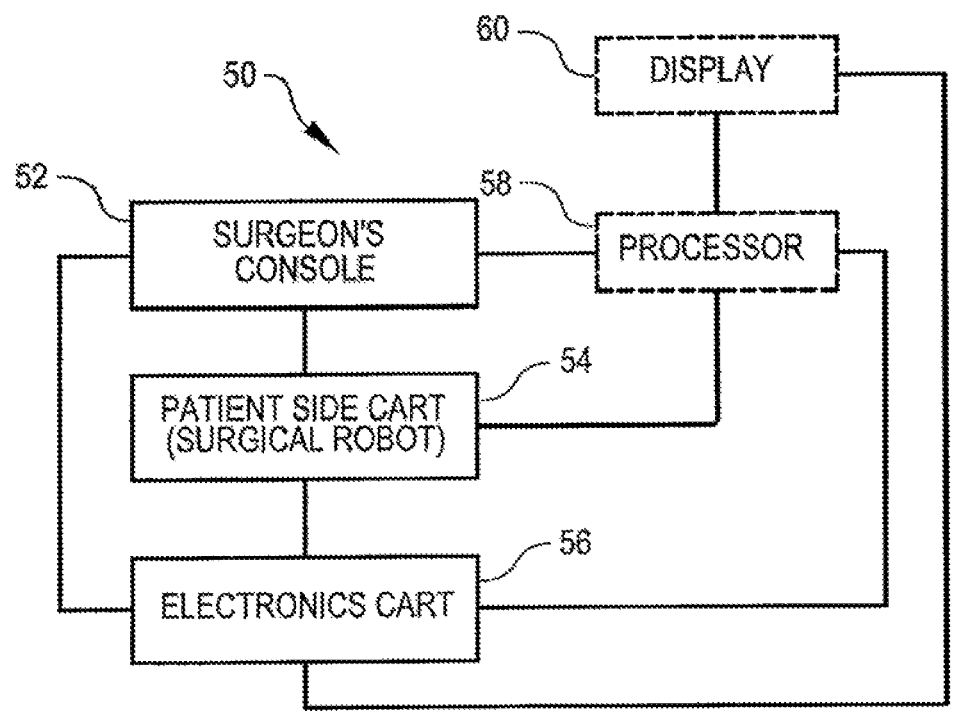
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a surgeon's console 52 (such as surgeon's console 16 in FIG. 1A) can be used by a surgeon to control a patient side cart (surgical robot) 54 (such as patient side cart 22 in FIG. 1A) during a minimally invasive procedure. The patient side cart 54 can use an imaging device, such as a stereoscopic endoscope, to capture images of the procedure site and output the captured images to an electronics cart 56 (such as the electronics cart 24 in FIG. 1A). As discussed above, the electronics cart 56 can process the captured images in a variety of ways prior to any subsequent display. For example, the electronics cart 56 can overlay the captured images with a virtual control interface prior to displaying the combined images to the surgeon via the surgeon's console 52. The patient side cart 54 can output the captured images for processing outside the electronics cart 56. For example, the patient side cart 54 can output the captured images to a processor 58, which can be used to process the captured images. The images can also be processed by a combination of the electronics cart 56 and the processor 58, which can be coupled together so as to process the captured images jointly, sequentially, and/or combinations thereof. One or more separate displays 60 can also be coupled with the processor 58 and/or the electronics cart 56 for local and/or remote display of images, such as images of the procedure site, or other related images.

MIRS system 50 in certain embodiments is a system for performing a minimally invasive diagnostic or surgical procedure on a patient including various components such as a surgeon's console 52, an electronics cart 56, and a patient side cart 54. However, it will be appreciated by those of ordinary skill in the art that the system could operate equally well by having fewer or a greater number of components than are illustrated in FIG. 1B. Thus, the depiction of the system 50 in FIG. 1B should be taken as being illustrative in nature, and not limiting to the scope of the disclosure.

Figure 2:
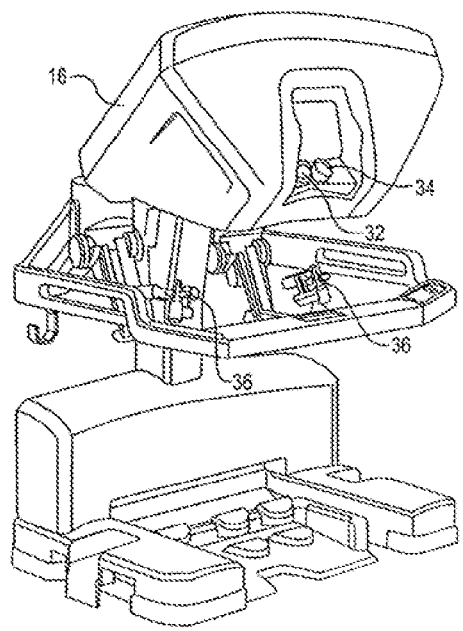
FIG. 2 is a perspective view of the surgeon console of FIG. 1A.

FIG. 2 is a perspective view of the surgeon's console 16. The surgeon's console 16 includes a left eye display 32 and a right eye display 34 for presenting the surgeon 18 with a coordinated stereo view of the surgical site that enables depth perception. The console 16 further includes one or more input control devices 36, which in turn cause the patient side cart 22 (shown in FIG. 1A) to manipulate one or more tools. The input control devices 36 can provide the same degrees of freedom, or more degrees of freedom, as their associated tools 26 (shown in FIG. 1A) so as to provide the surgeon with telepresence, or the perception that the input control devices 36 are integral with the tools 26 so that the surgeon has a strong sense of directly controlling the tools 26. To this end, position, force, and tactile feedback sensors (not shown) may be employed to transmit position, force, and tactile sensations from the tools 26 back to the surgeon's hands through the input control devices 36.

The surgeon's console 16 is usually located in the same room as the patient so that the surgeon may directly monitor the procedure, be physically present if necessary, and speak to an assistant directly rather than over the telephone or other communication medium. However, the surgeon can be located in a different room, a completely different building, or other remote location from the Patient allowing for remote surgical procedures.

Surgeon's console 16 in certain embodiments is a device for presenting the surgeon with information concerning the surgical site and receiving input information from the surgeon, and includes various components such as eyes displays and input control devices. However, it will be appreciated by those of ordinary skill in the art that the surgeon's console could operate equally well by having fewer or a greater number of components than are illustrated in FIG. 2. Thus, the depiction of the surgeon's console 16 in FIG. 2 should be taken as being illustrative in nature, and not limiting to the scope of the disclosure.

Figure 3:
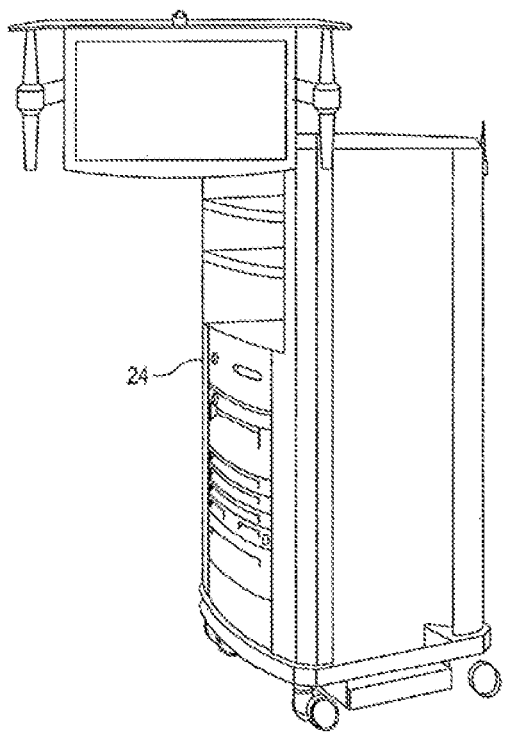
FIG. 3 is a perspective view of the electronics cart of FIG. 1A.

FIG. 3 is a perspective view of the electronics cart 24. The electronics cart 24 can be coupled with the imaging device 28 and can include a processor to process captured images for subsequent display, such as to a surgeon on the surgeon's console, or on another suitable display located locally and/or remotely. For example, where a stereoscopic endoscope is used, the electronics cart 24 can process the captured images so as to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

The electronics cart 24 in certain embodiments is a device for presenting information concerning a surgery to a surgical team and includes various components displays, processors, storage elements, etc. However, it will be appreciated by those of ordinary skill in the art that the electronics cart could operate equally well by having fewer or a greater number of components than are illustrated in FIG. 3. Thus, the depiction of the electronics cart 24 in FIG. 3 should be taken as being illustrative in nature, and not limiting to the scope of the disclosure.

Figure 4:
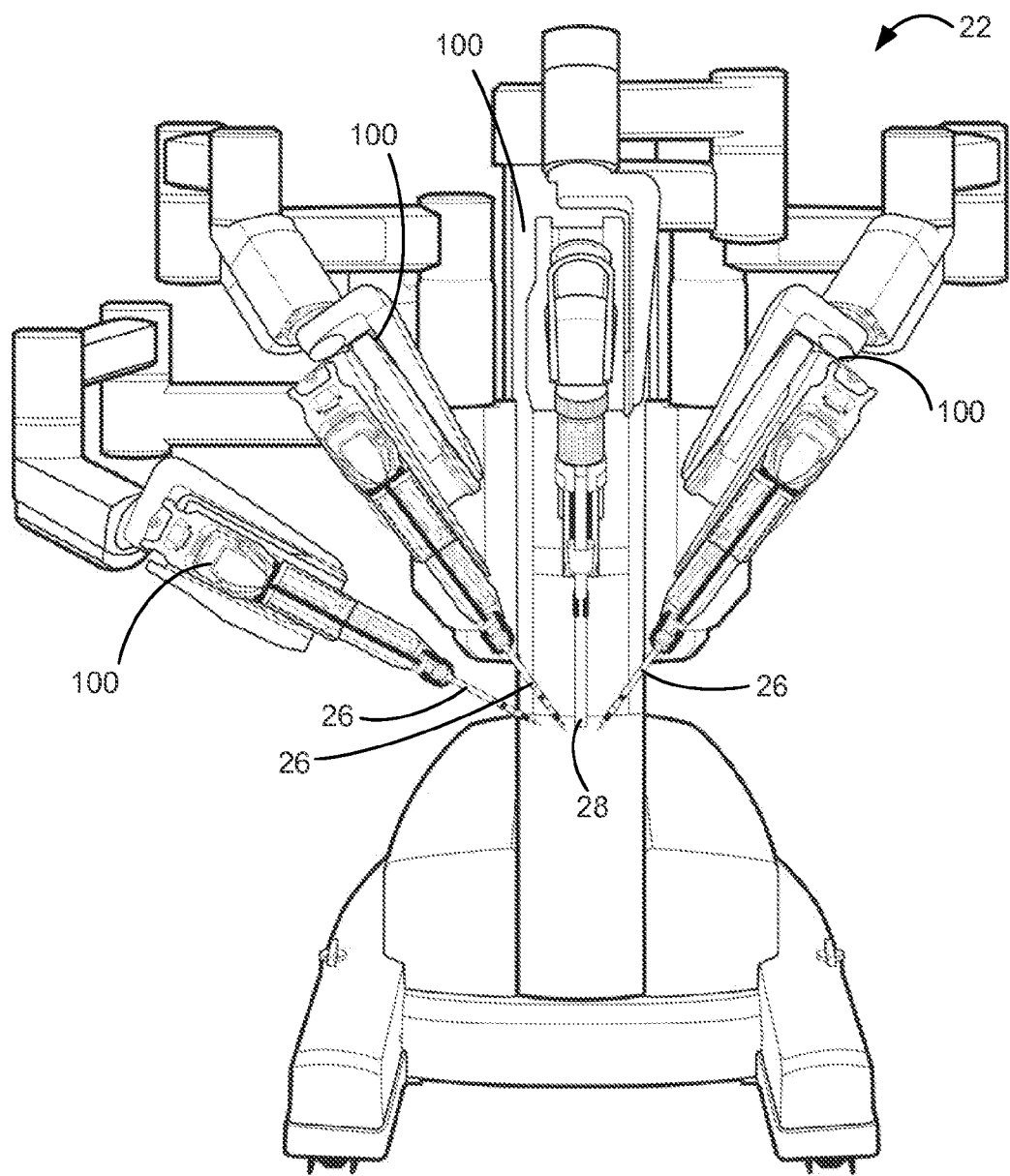
FIG. 4 is a perspective view of a patient side cart having a plurality of manipulator arms each supporting a surgical instrument.

FIG. 4 shows a patient side cart 22 having a plurality of manipulator arms 100 mounted to a support structure 110, each arm supporting a surgical instrument or tool 26 at a distal end of the manipulator arm. The patient side cart 22 shown includes four manipulator arms 100 which can be used to support either a surgical tool 26 or an imaging device 28, such as a stereoscopic endoscope used for the capture of images of the site of the procedure. The support structure 110 may include one or more elements suitable for supporting the manipulator arms 100, such as wheels, a base, legs, a spine, etc. In some embodiments, the support structure 110 may include electronic components such as processors, storage elements, etc., and in at least one embodiment includes a connector for mechanically coupling the manipulator arms 100 to the support structure 110 and for electrically coupling components of the manipulator arms 100 and/or tools 26 (e.g., motors or other actuators) to components of the support structure 110 (e.g., the processors, storage elements, etc.).

Manipulation of the tools 26 is provided by the robotic manipulator arms 100 having a number of robotic joints, where each joint provides a manipulator degree of freedom. The angle of each joint may be controlled by an actuator such as a motor or motor assembly, and in some embodiments the angle of each joint may be measured using one or more sensors (e.g., encoders, or potentiometers, or the like)

disposed on or proximate to each joint. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip a plier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allows the end effectors and the distal end of the shaft to be inserted distally into a surgical worksite through a minimally invasive aperture, often through an abdominal wall or the like. The surgical worksite may be insufflated, and movement of the end effectors within the patient will often be affected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside the patient 12 during a surgical procedure.

The patient side cart 22 in certain embodiments is a device for providing surgical tools for assisting in a surgical procedure on a patient, and may include various components such as a support structure 110, manipulator arms 100 and tools 26. However, it will be appreciated by those of ordinary skill in the art that the patient side cart could operate equally well by having fewer or a greater number of components than are illustrated in FIG. 4. Thus, the depiction of the patient side cart 22 in FIG. 4 should be taken as being illustrative in nature, and not limiting to the scope of the disclosure.

Figure 5:
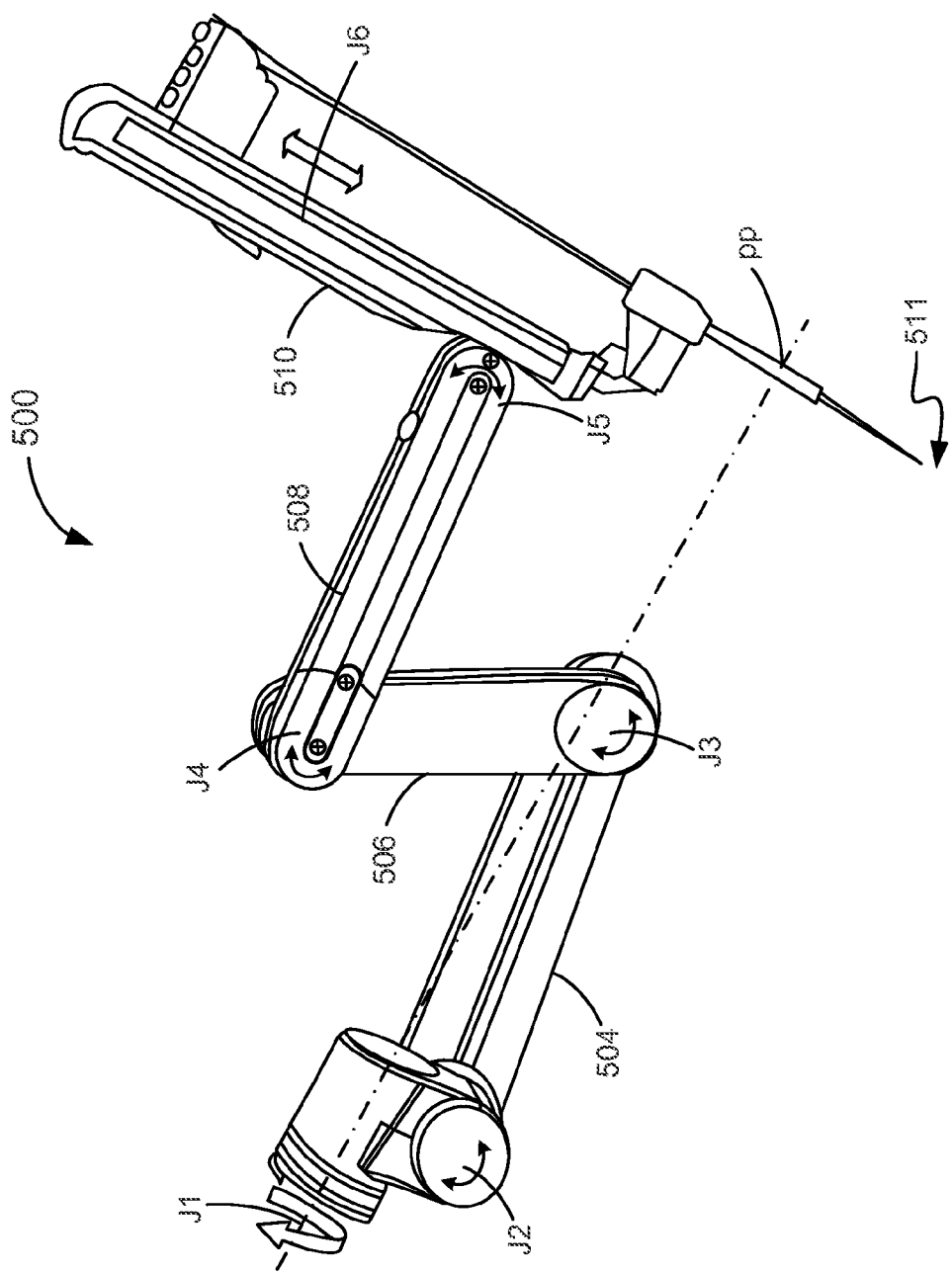
FIG. 5 is a perspective view of a manipulator arm in accordance with an embodiment.

An exemplary manipulator arm in accordance with some embodiments of the present invention can be understood with reference to FIG. 5. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an exemplary manipulator includes a plurality of joints having either redundant or non-redundant degrees of freedom, but is lacking at least one degree of freedom necessary to fully prescribe the position (i.e., location and orientation) of the end effector.

In many embodiments, such as that shown in FIG. 5, an exemplary manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator arm may be manipulated so as to control the position and/or orientation of a tool coupled thereto. In some embodiments, the joints of the manipulator, in combination, may have redundant degrees of freedom such that the joints of the manipulator arm can be driven into a range of differing configurations for a given end effector position. For example, if one or more additional, redundant degrees of freedom were added to the manipulator arm of FIG. 5, the resulting manipulator arm may be maneuvered into differing configurations while the distal instrument or tool 511 supported within the instrument holder 510 maintains a particular state, which may include a given position or velocity of the end effector. Regardless of whether a manipulator arm includes redundant degrees of freedom, in some embodiments the joints of the manipulator are not operable to independently control at least one of the six end effector degrees of freedom that fully define the position of the tool 511. For example, the manipulator may not be operable to cause the tool 511 to independently roll, pitch, yaw, and/or translate in one or more directions.

Describing the individual links of manipulator arm 500 of FIG. 5 along with the axes of rotation of the joints connecting the links as illustrated in FIG. 5, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, so as to provide a reduced width of the manipulator arm and improve patient clearance during maneuvering of the manipulator assembly. In many embodiments, the instrument holder 510 also includes additional joints, such as a prismatic joint J6 that facilitates axial movement of the instrument 511 through the minimally invasive aperture and facilitates attachment of the instrument holder 510 to a cannula through which the instrument 511 is slidably inserted. In some embodiments, even when combining the degrees of freedom of the instrument holder 510 with the rest of those of manipulator arm 500, the resulting degrees of freedom are still insufficient to provide at least one of the six degrees of freedom necessary to fully define the position of the tool 511.

The instrument 511 may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, instrument 511 includes a rotational joint J7 (not shown) near or proximal of the insertion point of the tool tip or the pivot point PP, which generally is disposed at the site of a minimally invasive aperture. A distal wrist of the instrument allows pivotal motion of an end effector of surgical tool 511 about instrument joints axes of one or more joints at the instrument wrist. An angle between end effector jaw elements may be controlled independently of the end effector location and orientation. Notwithstanding these additional kinematic degrees of freedom provided by the surgical tool 511, which may be considered to be part of the manipulator degrees of freedom, in some embodiments, even when combining the kinematic degrees of freedom of the surgical tool 511 with those of manipulator arm 500 (including, e.g., those of instrument holder 510), the resulting kinematic degrees of freedom are still insufficient to fully control the position of the tip of tool 511.

In a number of embodiments, the manipulator arm 500 may include connectors for mechanically and, in some embodiments, electrically, connecting to a support structure and a tool. In one embodiment, the manipulator arm 500 may include a support structure connector 512 that is shaped to engage with a corresponding connector on the support structure. The support structure connector 512 may include one or more elements for communicating information between elements of the support structure (e.g., one or more processors) and elements of the manipulator arm 500 (e.g., motors and/or sensors). For example, the support structure connector 512 may include electrical and/or optical components coupled to the motors, sensors, and/or other elements of the manipulator arm 500.

In another embodiment, the manipulator arm 500 may include a tool connector 514 that is shaped to engage with a corresponding connector on the tool. The tool connector 512 may include one or more elements for communicating information between elements of the tool (e.g., motors or other actuators, sensors, etc.) and elements of the manipulator arm 500 (e.g., electrical and/or optical conductors in the links, electrical and/or optical components of the support structure connector 512, etc.). For example, the manipulator arm 500 may include conductors (e.g., wires or optical fibers) arranged between and coupled to one or more components of the support structure connector 512 and the tool connector 512. The tool connector 512 may then also include electrical and/or optical components for communicating information with an attached tool, thereby facilitating information to be communicated between the support structure and a connected tool. In some embodiments, the tool connector 514 may include one or more output couplers (not shown) that may mechanically engage with corresponding input couplers of a tool, where movement (e.g., rotation, translation, etc.) of the output coupler causes a corresponding movement of the input coupler via the mechanical engagement.

The manipulator arm 500 in certain embodiments is a mechanical body for holding and controlling a tool, and may include a number of links and joints. However, it will be appreciated by those of ordinary skill in the art that the manipulator arm could operate equally well by having fewer or a greater number of components than are illustrated in FIG. 5. Thus, the depiction of the manipulator arm 500 in FIG. 5 should be taken as being illustrative in nature, and not limiting to the scope of the disclosure.

Figure 6A:
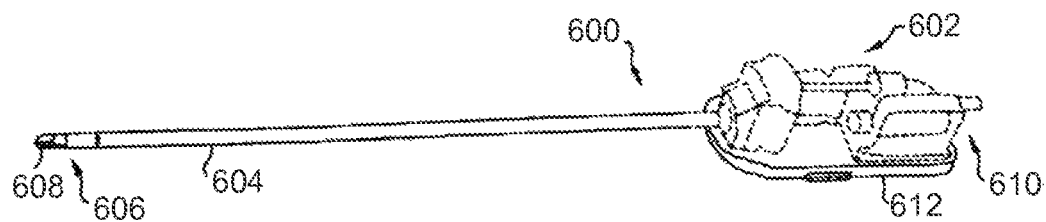
FIG. 6A is a perspective view of a robotic surgery tool that includes an end effector having opposing clamping jaws in accordance with an embodiment.

FIG. 6A shows a surgical tool 600 that includes a proximal chassis 602, an instrument shaft 604, and a distal end effector 606 having a jaw 608 that can be articulated to grip a patient tissue. The proximal chassis 602 includes a frame 612 and, in some embodiments, a spring assembly 610, that is shaped to engage with the distal end of a manipulator arm (e.g., shaped to connect to the tool connector 514 described with reference to FIG. 5). The proximal chassis 602 may also include an input coupler that is configured to interface with and be driven by an output coupler of the manipulator arm. The input coupler is drivingly coupled with an input link of a spring assembly 610. The spring assembly 610 is mounted to the frame 612 of the proximal chassis 602 and includes an output link that is drivingly coupled with a drive shaft that is disposed within the instrument shaft 604. The drive shaft is drivingly coupled with the jaw 608. In some embodiments, the proximal chassis 602 may also include electrical and/or optical elements for electrically and/or optically coupling to corresponding elements of the manipulator arm (e.g., corresponding elements of the tool connector 514). In this fashion, information may be communicated between elements of the tool 600 (e.g., motors, actuators, sensors, etc.) and elements of the manipulator arm.

In accordance with some embodiments and as shown in FIG. 6A, the surgical tool 600 may not include any degrees of freedom for altering a position of the end effector 606. In other embodiments, the surgical tool 600 may include one or more joints for adding degrees of freedom for altering the position of the end effector 606. For example, the instrument shaft 604 may include joints for changing a pitch and/or yaw of the end effector 606. Further, in some embodiments and as shown in FIG. 6A, the surgical tool 600 may include one or more degrees of freedom for actuating the end effector 606. For example, the spring assembly 610 may be operable to actuate the jaw 608. Additional characteristics of surgical tool 600, as well as other surgical tools, are described in commonly-owned U.S. application Ser. No. 13/297,158, filed Nov. 15, 2011, entitled "Method for Passively Decoupling Torque Applied By a Remote Actuator Into an Independently Rotating Member," the disclosure of which is incorporated herein by reference in its entirety.

Figure 6B:
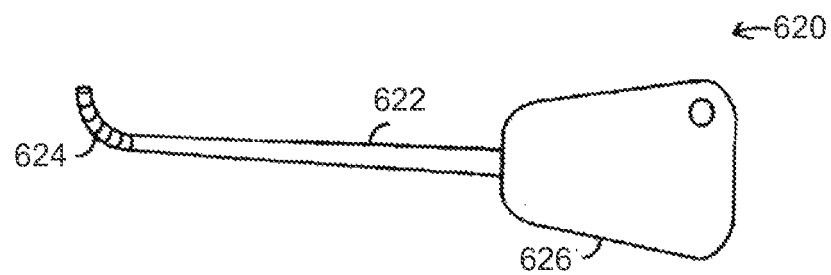
FIG. 6B illustrates a wristed endoscope in accordance with an embodiment.

FIG. 6B illustrates a wristed endoscope 620 that may, in some embodiments, be used in robotic minimally invasive surgery. The endoscope 620 includes an elongate shaft 622 and a flexible wrist 624 located at the working end of the shaft 622. A housing 626 allows the surgical instrument 620 to releasably couple to a manipulator located at the opposite end of the shaft 624. An endoscopic camera lens is implemented at the distal end of the flexible wrist 624. A lumen (not shown) runs along the length of the shaft 622 which connects the distal end of the flexible wrist 624 to the housing 626. In a "fiber scope" embodiment, imaging sensor(s) of the endoscope 620, such as charge coupled devices (CCDs), may be mounted inside the housing 626 with connected optical fibers running inside the lumen along the length of the shaft 622 and ending at substantially the distal end of the flexible wrist 624. In an alternate "chip-on-a-stick" embodiment, the imaging sensor(s) of the endoscope 620 may be mounted at the distal end of the flexible wrist 624. The imaging sensor(s) may be two-dimensional or three-dimensional.

In some embodiments, the flexible wrist 624 may have at least one degree of freedom to allow the endoscope 620 to articulate and maneuver easily around internal body tissues, organs, etc. to reach a desired destination (e.g., epicardial or myocardial tissue). The housing 626 may house a drive mechanism for articulating the distal portion of the flexible wrist 624. The drive mechanism may be cable-drive, gear-drive, belt drive, or another type of drive mechanism suitable to drive the flexible wrist 624 along its degree(s) of freedom. For example, in one embodiment, the flexible wrist 624 may have two translation degrees of freedom and the shaft 622 may be operable to rotate around an axis along the length of the shaft 622. In some medical procedures, the articulate endoscope 620 maneuvers and articulates around internal organs, tissues, etc. to acquire visual images of hard-to-see and/or hard-to-reach places. Additional characteristics of the endoscope 620, as well as other surgical tools, are described in commonly-owned U.S. application Ser. No. 11/319,011, filed Dec. 27, 2005, entitled "Articulate and Swapable Endoscope for a Surgical Robot," the disclosure of which is incorporated herein by reference in its entirety.

Figure 6C:
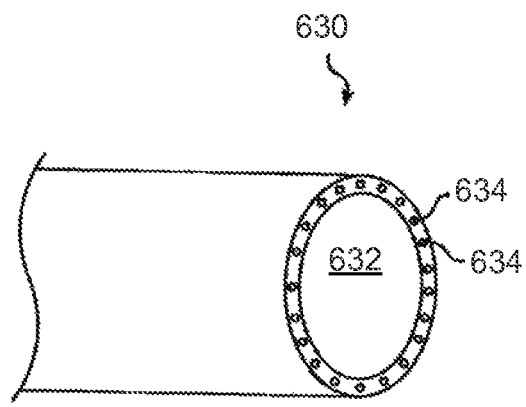
FIG. 6C is a perspective view of the distal end of an overtube with suction ports in accordance with an embodiment.

In at least one embodiment, the housing 626 may be shaped to engage with the distal end of a manipulator arm (e.g., shaped to connect to the tool connector 514 with reference to FIG. 5). Further, the housing 626 may include electrical and/or optical elements for electrically and/or optically coupling to corresponding elements of the manipulator arm. In this fashion, information may be communicated between elements of the tool 620 (e.g., motors, actuators, sensors, etc.) and elements of the manipulator arm. FIG. 6C is a perspective view of the distal end of an overtube with suction ports. The overtube 630 defines an instrument lumen 632 which extends through the overtube 630 to permit passage of an instrument. The overtube 630 further comprises one or more suction passages 634 which are coupled to a vacuum source. The overtube 630 may, in various embodiments, be formed out of any of a variety of materials suitable for surgical use and may be provided with any of variety of stiffnesses. For example, the overtube 630 may comprise a substantially rigid material, may comprise a flexible material, or may comprise a combination of one or more substantially rigid portions and one or more flexible portions to provide a bendable structure. The cross-sectional shape of the overtube 630 may also vary. In the illustrated embodiment, the overtube 630 has a substantially circular cross-sectional shape and is made out of polyurethane. In other embodiments, other cross-sectional shapes may be used, such as, e.g., oval, rectangular, triangular, etc., depending on the application.

In the illustrated embodiment, the suction passages 634 comprises a plurality of vacuum lumens within the wall of the overtube 630, with each vacuum lumen being coupled to the vacuum source (not shown). The vacuum source may be operated to create a vacuum pressure in each suction passage 634, thereby creating a suction force onto a tissue surface which the suction passages 634 are in contact with. As a result of this suction force, the overtube 630 will be attached to the tissue surface. If the vacuum pressure is discontinued, the tissue surface will be released and the overtube 630 will no longer be attached to the tissue. Accordingly, by controllably providing a suction force via the suction passages 634, the overtube 630 can be releasably attached to patient's tissue surface. A surgical instrument, such as an irrigation tool, cutting tool, etc., may then be inserted through the instrument lumen 200 to treat tissue disposed within the instrument lumen 632.

In accordance with some embodiments, the overtube 630 may be made of substantially rigid material and not include any degrees of freedom for altering a position of the overtube 630. In other embodiments, the overtube 630 may include one or more joints for adding degrees of freedom for altering the position of the distal end of the overtube 630. For example, the overtube 630 may include joints for changing a pitch and/or yaw of the distal end of the overtube 630. Further, in some embodiments, the overtube 630 may include one or more degrees of freedom for actuating functionality of the overtube 630. For example, a vacuum source (not shown) may be operable to create or remove a vacuum pressure in one or more suction passages 634. Additional characteristics of the overtube 630, as well as other surgical tools, are described in commonly-owned U.S. application Ser. No. 11/618,374, filed Dec. 29, 2006, entitled "Vacuum Stabilized Overtube for Endoscopic Surgery," the disclosure of which is incorporated herein by reference in its entirety.

Further, in at least one embodiment, the overtube 630 may be provided in or coupled to a housing (not shown) that may be shaped to engage with the distal end of a manipulator arm (e.g., shaped to connect to the tool connector 514 with reference to FIG. 5). Further, the housing may include electrical and/or optical elements for electrically and/or optically coupling to corresponding elements of the manipulator arm. In this fashion, information may be communicated between elements of the overtube 630 (e.g., motors, actuators, sensors, etc.) and elements of the manipulator arm.

Figure 6D:
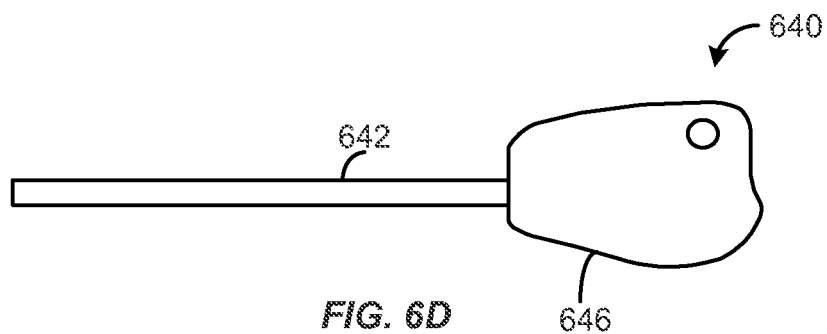
FIG. 6D illustrates a non-wristed endoscope in accordance with an embodiment.

FIG. 6D illustrates a non-wristed endoscope 640 that may, in some embodiments, be used in robotic minimally invasive surgery. The non-wristed endoscope 640 is similar to the wristed endoscope 620 depicted in and discussed with reference to FIG. 6B, and thus similarly includes a housing 646 and a shaft 622. The difference is that the non-wristed endoscope 640 does not include a flexible wrist. The non-wristed endoscope has a reduced number of degrees of freedom compared to the wristed endoscope, and in this particular example, non-wristed endoscope 640 does not have a wrist pitch or wrist yaw.

The surgical tool 600, endoscope 620, and overtube 30 are various tools that include a variety of components. However, it will be appreciated by those of ordinary skill in the art that these tools could operate equally well by having fewer or a greater number of components than are illustrated in FIGS. 6A to 6C. Further, it would will also be appreciated that other tools may also or alternatively be used, such as gripping devices, electrosurgical paddles, vacuums, irrigators, staplers, scissors, knifes, etc. Thus, the depiction of surgical tools in FIGS. 6A to 6C should be taken as being illustrative in nature, and not limiting to the scope of the disclosure.

Figure 7A:
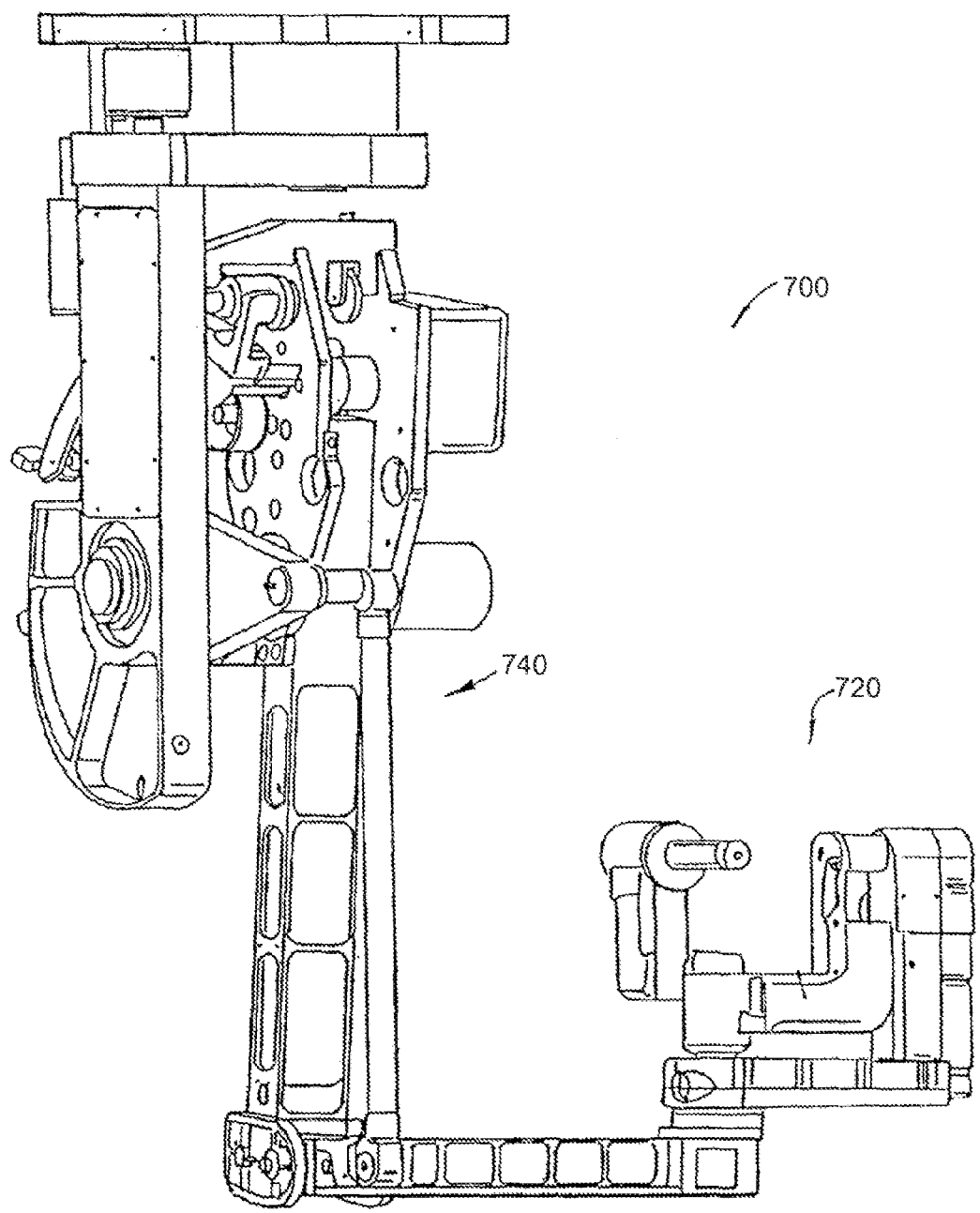
FIG. 7A is a perspective view of a master control input device in accordance with an embodiment.

FIG. 7A is a perspective view of a master control input device 700 that may be part of a surgeon's console 16 (FIG. 1A) in accordance with an embodiment. The master control 700 includes a gimbal or wrist 720 that is operatively coupled to an articulated arm 740.

Master control input device 700 has a number of degrees of freedom and is operable to control a manipulator assembly (e.g., manipulator arm 500 of FIG. 5). The degrees of freedom of input device 700 includes kinematic degrees of freedom defined by joints of input device 700, used to control the kinematics of manipulator arm 500, and may also include actuation degrees of freedom used to actuate a tool (e.g., instrument 511) connected to manipulator arm 500. Input device 700, like a tool of manipulator arm 500, may also be considered to have an end effector (or, more generally, a control frame) associated therewith, which itself has a number of kinematic degrees of freedom.

In some embodiments, input device 700 may have a sufficient number of degrees of freedom to fully control the position of an end effector. For example, the input device 700 may have six degrees of freedom that may independently control the three translation and three orientation degrees of freedom of an end effector of the instrument 511. In some cases, even though the input device 700 has such a sufficient number of degrees of freedom, the manipulator assembly (e.g., manipulator arm 500) has a number of degrees of freedom that is insufficient to independently control the three translation and three orientation degrees of freedom of the end effector. For example, the manipulator arm 500 may have only five degrees of freedom.

In some embodiments, the input device 700 may have additional degrees of freedom, which may be degrees of freedom operable to control the position of the end effector (e.g., a redundant degree of freedom), and/or may be degrees of freedom operable to actuate the instrument 26 (e.g., turning on or off suction or irrigation, actuating a clamp, engaging a staple with tissue, etc.). An input device having additional degrees of freedom is described in commonly-owned U.S. application Ser. No. 10/121,283, filed Apr. 11, 2002, entitled "Master Having Redundant Degrees of Freedom," the disclosure of which is incorporated herein by reference in its entirety. Further, in at least one embodiment, the instrument 511, either alone or in combination with a manipulator arm 500, may have additional kinematic degrees of freedom that add to the degrees of freedom of the manipulator arm 500. For example, the instrument 511 may have joints for controlling the position of the end effector. In some cases, even when combining the kinematic degrees of freedom of the manipulator arm 500 with the kinematic degrees of freedom of the instrument, the position of the end effector may not be fully controlled. This may be, e.g., due to the joints of the instrument 511 merely adding kinematic degrees of freedom that are redundant to those already provided by the manipulator arm 500. In some embodiments, the instrument 511 may have additional actuation degrees of freedom for actuating the instrument 511 (e.g., turning on or off suction or irrigation, actuating a clamp, engaging a staple with tissue, etc.).

To facilitate control of the instrument 511, the master control input device 700 may include one or more actuators or motors and, in some embodiments, sensors for each of a plurality of joints of the master control input device 700. The motors and sensors of the input device 700 may be operatively linked to the motors and sensors associated with the manipulator arms (e.g., arm 500 of FIG. 5) and the surgical instruments mounted thereon (e.g., instrument 511 of FIG. 5) via a control system disposed in, e.g., the surgeon's console 16, the electronics cart 24, and/or the patient cart 22, and/or any other element of MIRS system 10 (FIG. 1). The control system may include one or more processors for effecting control between the master control device input and responsive robotic arm and surgical instrument output and for effecting control between robotic arm and surgical instrument input and responsive master control output in the case of, e.g., force feedback.

Figure 7B:
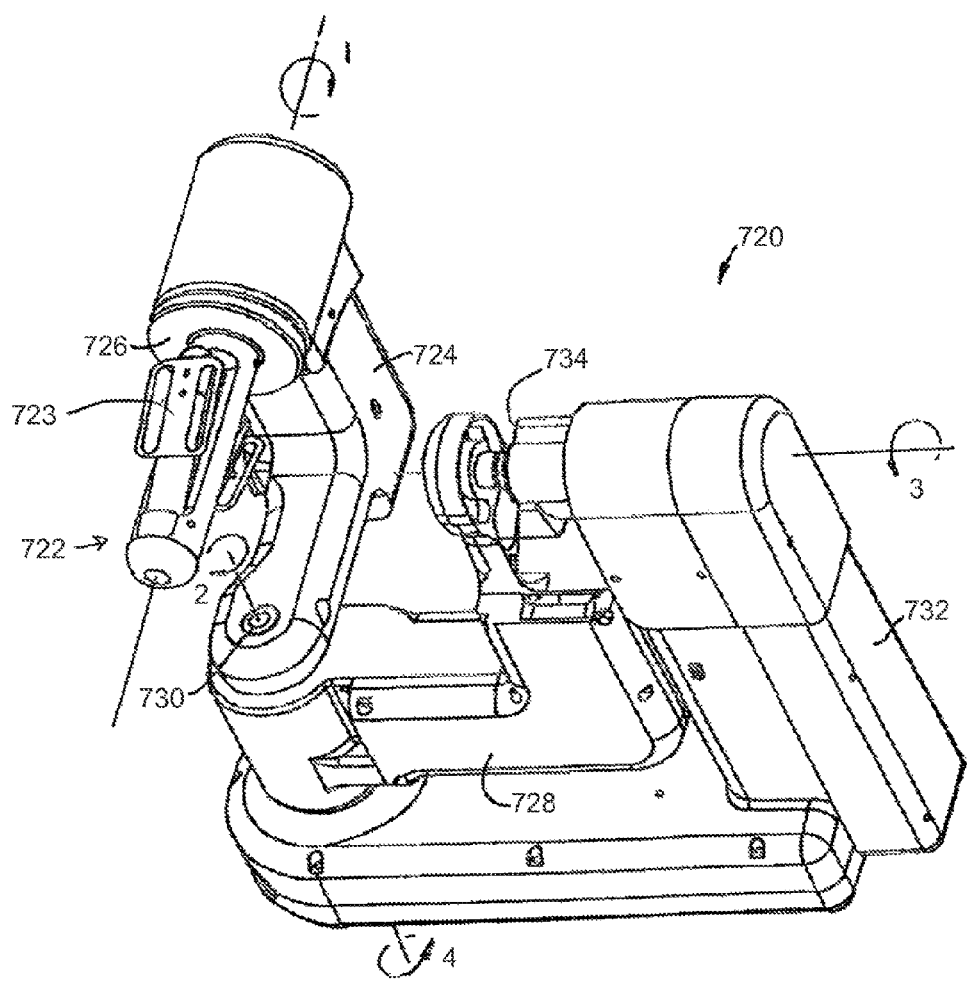
FIG. 7B is a perspective view of a gimbal or wrist of the input device of FIG. 7A.

FIG. 7B is a perspective view of a gimbal or wrist 720 according to an embodiment. According to this embodiment, gimbal or wrist 720 allows rotation of an actuatable handle 722 about three axes, axis 1, axis 2, and axis 3. More specifically, the handle 722 is coupled to a first elbow-shaped link 724 by a first pivotal joint 726. The first link 724 is coupled to a second elbow-shaped link 728 by a second pivotal joint 730. The second link 728 is pivotally coupled to a third elbow-shaped link 732 by a third pivotal joint 734. The gimbal or wrist 720 may be mounted on an articulated arm 740 (as shown in FIG. 7A) at axis 4 such that the gimbal or wrist 720 can displace angularly about axis 4. By way of such links and joints, the gimbal or wrist 720 may provide a number of kinematic degrees of freedom for the control input device 700 and be operable to control one or more of the end effector degrees of freedom.

In some embodiments, the handle 722 may include a pair of grip members 723 for actuating a tool or end effector. For example, by opening or closing the grip members 723, the jaw 608 of the end effector 606 (FIG. 6) may similarly be opened or closed. In other embodiments, one or more input elements of the handle 722 and/or of other elements of the surgeon's console 16 may be operable to actuate one or more degrees of freedom of the instrument 511 other than degrees of freedom for controlling the position of the instrument 26. For example, the surgeon's console 16 may include a foot pedal coupled to the control system for activating and deactivating a vacuum pressure.

In some embodiments, the joints of the gimbal or wrist 720 may be operatively connected to actuators, e.g., electric motors, or the like, to provide for, e.g., force feedback, gravity compensation, and/or the like. Furthermore, sensors such as encoders, potentiometers, and the like, may be positioned on or proximate to each joint of the gimbal or wrist 720, so as to enable joint positions of the gimbal or wrist 720 to be determined by the control system.

Figure 7C:
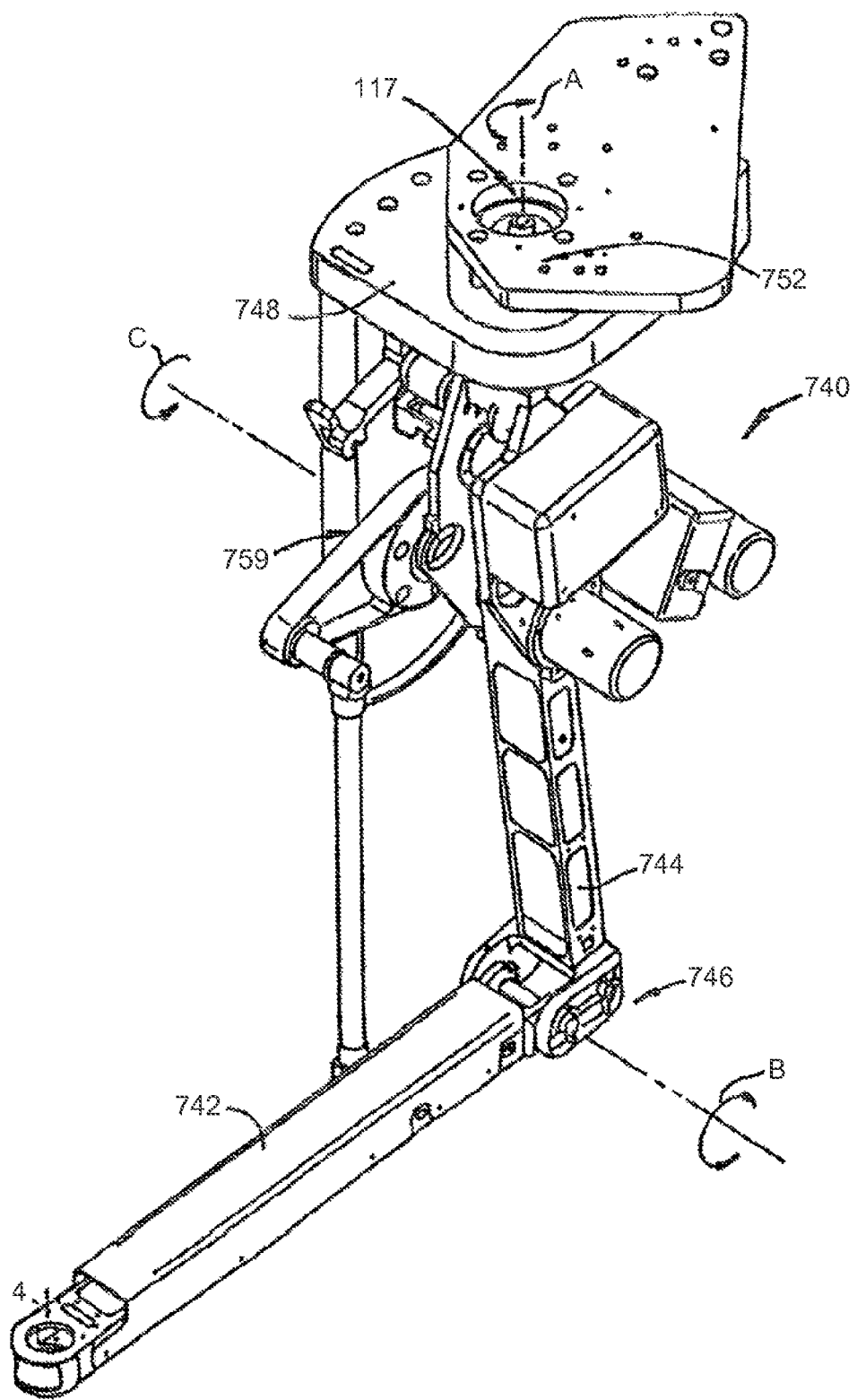
FIG. 7C is a perspective view of an articulated arm of the input device of FIG. 7A.

FIG. 7C is a perspective view of an articulated arm 740 according to an embodiment. According to this embodiment, the articulated arm 740 allows rotation of a gimbal or wrist 720 (FIG. 7B) about three axes, axis A, axis B, and axis C. More specifically, the gimbal or wrist 720 may be mounted on the arm 740 at axis 4 as previously described with reference to FIG. 7B. The gimbal or wrist 720 is coupled to a first link 742 which is pivotally coupled to a second link 744 by a first pivotal joint 746. The second link 744 is pivotally coupled to a third link 748 by a second pivotal joint 750. The third link 748 may be pivotally coupled to the surgeon's console 16 (FIG. 1) by a third pivotal joint 752. By way of such links and joints, the articulated arm 740 may provide a number of kinematic degrees of freedom for the control input device 700 and be operable to control one or more of the kinematic degrees of freedom of a manipulator assembly to thereby control the position of an instrument (e.g., instrument 511 of FIG. 5).

In some embodiments, the joints of the articulated arm 740 may be operatively connected to actuators, e.g., electric motors, or the like, to provide for, e.g., force feedback, gravity compensation, and/or the like. Furthermore, sensors such as encoders, potentiometers, and the like, may be positioned on or proximate to each joint of the articulated arm 740, so as to enable joint positions of the articulated arm 740 to be determined by the control system.

Input device 700 in certain embodiments is a device for receiving inputs from a surgeon or other operator and includes various components such as a gimbal or wrist 720 and an articulated arm 740. However, it will be appreciated by those of ordinary skill in the art that the input device could operate equally well by having fewer or a greater number of components than are illustrated in FIGS. 7A to 7C. Thus, the depiction of the input device 700 in FIGS. 7A to 7C should be taken as being illustrative in nature, and not limiting to the scope of the disclosure.

Figure 8A:
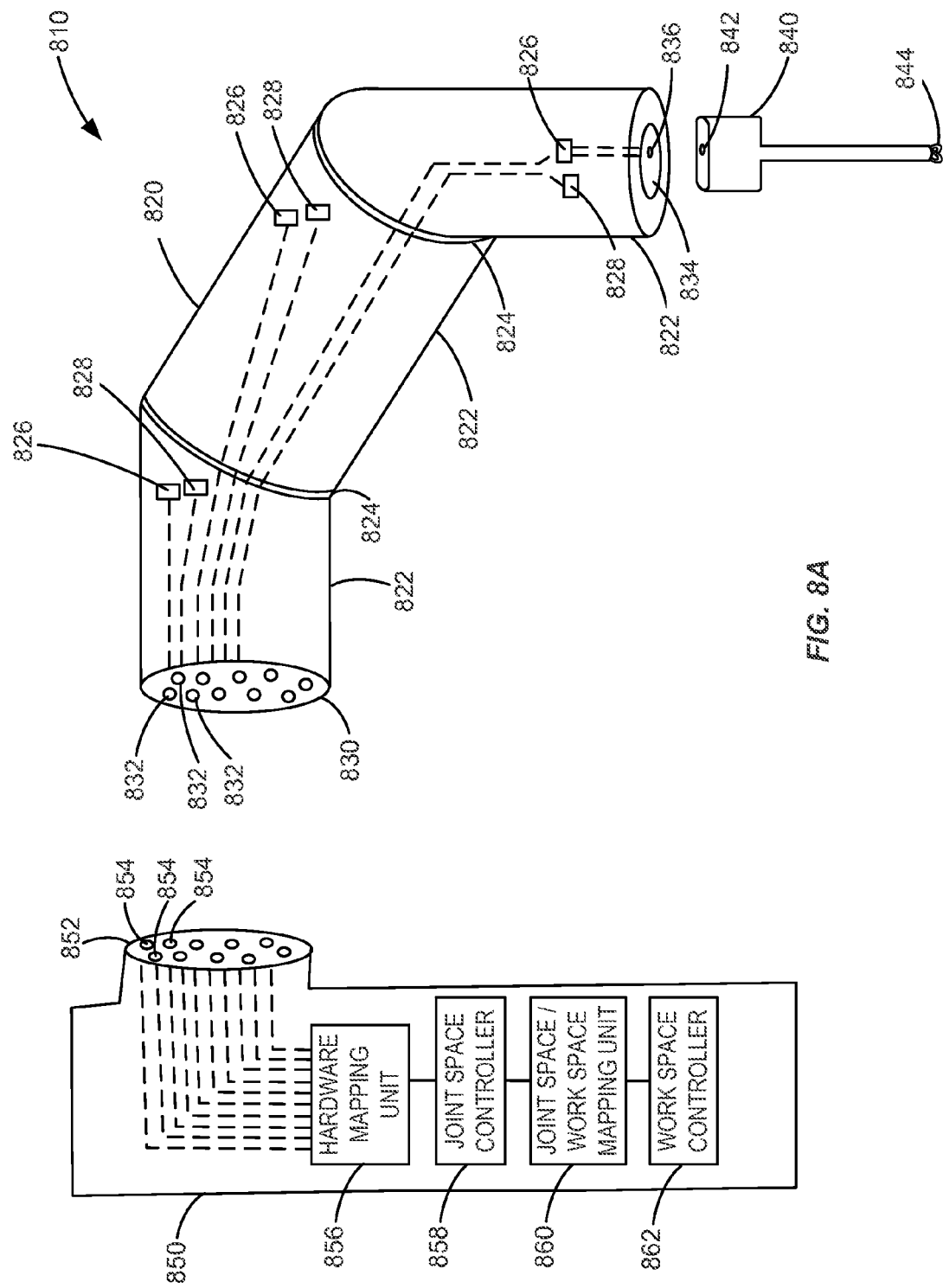
FIG. 8A is part of a robotic system including a manipulator assembly and a support structure according to a first embodiment.

FIG. 8A is part of a robotic system including a manipulator assembly 810 and a support structure 850 according to a first embodiment. The manipulator assembly 810 includes a manipulator 820 and a tool 840, where the manipulator 820 is disposed between and may be connected to each of the support structure 850 and the tool 840.

The manipulator 820 includes a plurality of links 822 coupled together by joints 824. The manipulator 820 may also include a number of actuators 826 such as motors, and a number of sensors 828 such as potentiometers, where each joint may be associated with an actuator and/or a sensor. The actuator may be operable to control a degree of freedom of the manipulator, such as by controlling one or more joints to rotate, translate, etc. Further, the sensor may be operable to measure a position or state of each of a corresponding joint.

The manipulator 820 also includes a connector 830 at a proximal end that is shaped to engage a corresponding connector of the support structure 850, the connector 830 forming a mechanical interface operable to mechanically couple the manipulator arm 820 to the support structure. The connector 830 may also include electrical and/or optical contacts 832 that are positioned, sized, and shaped to engage corresponding contacts of the support structure 850, whereby the electrical and/or optical contacts 832 may form an electrical interface operable to communicate information between elements of the manipulator assembly 810 and elements of the support structure 850. The contacts 832 may be directly or indirectly coupled (e.g., electrically, optically, etc.) to elements of the manipulator 820 such as actuators 826 and/or sensors 828. In one embodiment, each contact 832 is coupled to one actuator 826 or sensor 828. Accordingly, information may be communicated between elements of the manipulator 820 (e.g., the actuators and sensors 828) and elements of the support structure 850. For example, instructions may be communicated from the support structure to the motors 826 to cause the motors to control corresponding degrees of freedom of the manipulator arm 820, and position/state information may be communicated from the sensors 828 to the elements of the support structure 850.

In some embodiments, the manipulator 820 may also include a connector 834 at a distal end that is shaped to engage a corresponding connector of the tool 840, the connector 834 forming a mechanical interface operable to mechanically couple the manipulator arm 820 to the tool 840. The connector 834 may also include one or more mechanical elements 836 that may be sized and shaped to engage with corresponding mechanical elements 842 included in the tool 840. The mechanical element 836 may be actuated or otherwise controlled by an actuator 826, such that upon engaging the tool 840 with the manipulator 820, actuation of the mechanical element 836 may cause actuation of the corresponding mechanical element 842 in the tool 840. The corresponding mechanical element 842 in the tool 840 may be operable to manipulate a degree of freedom of the tool 840 (e.g., actuating an end effector 844 of the tool 840. In some embodiments, one or more sensors 828 included in or disposed on the manipulator 820 may be operable to sense a position and/or state of the tool 840.

Support structure 850 includes a connector 852 that is shaped to engage a corresponding connector (e.g., connector 830) of the manipulator 820. The connector 852 may also include electrical and/or optical contacts 854 that are positioned, sized, and shaped to engage corresponding contacts (e.g., contacts 832) of the manipulator 820, whereby the electrical and/or optical contacts 854 may form an electrical interface operable to communicate information between elements of the manipulator arm 820 and elements of the tool 840. The contacts 854 may be directly or indirectly coupled (e.g., electrically, optically, etc.) to elements of the support structure 850 such as a hardware mapping unit 856, a joint space controller 858, a joint space work space mapping unit 860, and/or a work space controller 862.

In one embodiment, the hardware mapping unit 856 is operable to map signals between a manipulator assembly 810 (e.g., signals to/from actuators, sensors, etc. of the manipulator assembly via, e.g., electrical/optical contacts 854) and joint space controller 858. The hardware mapping unit 856 may include (and/or acquire) a specific map for each of a plurality of different manipulator assemblies, such as different manipulator arms 820 and/or different tools 840. In some embodiments, the hardware mapping unit 856 may include input maps and output maps. In one embodiment, the input maps and output maps may be different from one another. For example, an actuator 826 and a sensor 828 may each communicate with the support structure 850 via a single contact 854. Accordingly, the input map may map signals from the contacts 854 corresponding to sensors 828 to the joint space controller 858, and the output map may map signals from the joint space controller 858 to the contacts 854 corresponding to actuators 826. In another embodiment, the input maps and output maps may be the same as one another. For example, an actuator 826 and a sensor 826 may both communicate with the support structure 850 via a single contact 854. Accordingly, the input map and output map may be the same as they may map input and output interface elements of the joint space controller 858 to the same contact 854.

The joint space controller 858 may be a processor operable to perform calculations and execute a number of algorithms in joint space. For example, the joint space controller 858 may be operable to execute joint motion algorithms, comparisons of redundant sensors on each joint, motor health algorithms, etc.

The joint space controller 858 may receive input information from a number of different sources. For example, the joint space controller 858 may receive outputs from the work space controller 862 via the joint space work space mapping unit 860. For another example, the joint space controller 858 may receive inputs (e.g., sensor signals from sensors 826) from the manipulator 820 via the hardware mapping unit 856. For yet another example, the joint space controller 858 may receive inputs from an input device such as a master control input device (FIGS. 7A to 7C). Further, the joint space controller 858 may provide output information to a number of different destinations. For example, the joint space controller 858 may output information (e.g., control information) to the manipulator 820 (e.g., to actuators 826) via the hardware mapping unit 856. For another example, the joint space controller 858 may provide outputs to the work space controller 865 via the joint space work space mapping unit 860 for further processing. For yet another example, the joint space controller 858 may provide outputs to an input device such as a master control input device (FIGS. 7A to 7C).

The joint space work space mapping unit 860 is operable to map signals between the joint space controller 858 (e.g., signals representing desired or actual positions or states of the degrees of the freedom of the manipulator assembly 810) and the work space controller 862. The joint space work space mapping unit 860 may include a specific map for each of a plurality of different manipulator assemblies, such as different manipulator arms 820 and/or different tools 840. Accordingly, the joint space work space mapping unit 860 may be operable to map input/output interface elements of the joint space controller 858 to input/output interface elements of the work space controller 862 based on the particular manipulator assembly 810 connected to the support structure 850.

The work space controller 862 may be a processor operable to perform calculations and execute a number of algorithms in a multi-dimension (e.g., 3 dimensional) work space. This may be, e.g., a work space based on polar coordinates, Cartesian coordinates, or other type of coordinate system. The work space controller 862 may be operable to execute a variety of algorithms. For example, the work space controller 865 may be operable to perform forward kinematics, inverse kinematics, determine the work space error between desired and actual positions/orientations, etc.

The work space controller 862 may receive input information from a number of different sources. For example, the work space controller 862 may receive outputs from the joint space controller 858 via the joint space work space mapping unit 860. For another example, the work space controller 862 may receive inputs from an input device such as a master control input device (FIGS. 7A to 7C). Further, the work space controller 862 may provide output information to a number of different destinations. For example, the work space controller 862 may output information (e.g., control information) to joint space controller 858 via the joint space work space mapping unit 860. For yet another example, the work space controller 862 may provide outputs to an input device such as a master control input device (FIGS. 7A to 7C).

In at least one embodiment, a plurality of different tools may be provided, having the same or different number of degrees of freedom. The tools may all have the same mechanical interface so that they may all be attached to the same manipulator arm and, in some cases, switched during a surgical procedure. Further, a plurality of different manipulator arms may be provided, having the same or different degrees of freedom. The manipulator arms may also have the same mechanical interfaces so that they may all be attached to the same support structure and to the same tools and, in some cases, may be switched during or between surgical procedures.

In one embodiment, the controllers and/or mapping units described herein may be individual processors coupled to individual or a common information storage element. In other embodiments, the controllers and/or mapping units described herein may be implemented as software code on a tangible non-transitory computer readable storage medium. Although these elements are described as being part of support structure 850, in some embodiments some or all of these elements may be included in other parts of the robotic system, such as in a control system disposed in, e.g., the manipulator 820, the surgeon's console 16, the electronics cart 24, and/or the patient cart 22, and/or any other element of MIRS system 10 (FIG. 1).

Figure 8B:
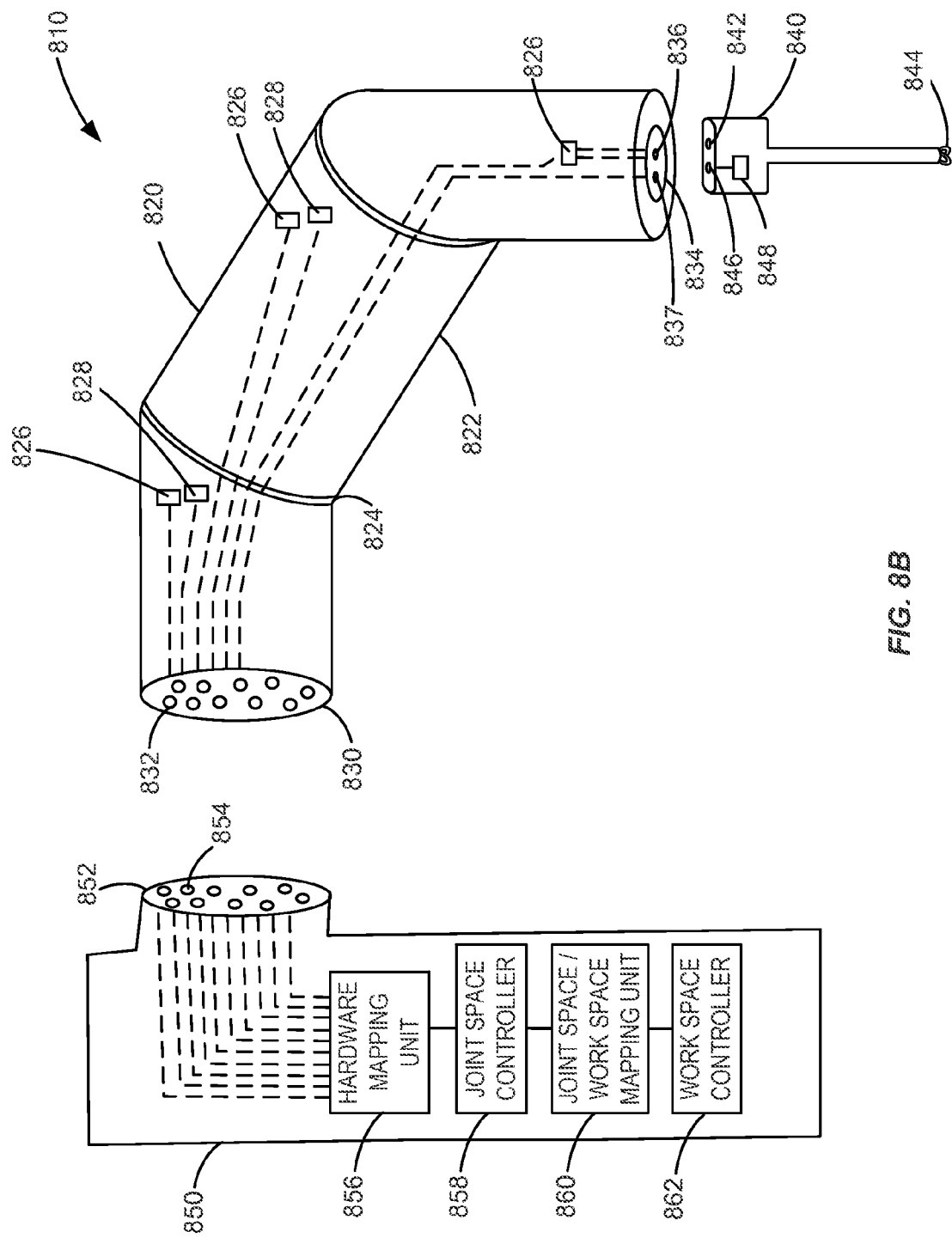
FIG. 8B is part of a robotic system including a manipulator assembly and a support structure according to a second embodiment.

FIG. 8B is part of a robotic system including a manipulator assembly 810 and a support structure 850 according to a second embodiment. The manipulator assembly 810 and support structure 850 in this embodiment are similar to that discussed with reference to FIG. 8A, and thus the structures and functions discussed with reference to FIG. 8A are equally applicable for this embodiment.

In accordance with this embodiment, however, the tool 840 includes an electrical/optical contact 846 coupled to and operable to communicate information with an internal element 848 of the tool 840. The element 848 may be, e.g., an actuator such as actuator 826 and/or a sensor such as sensor 828. The actuator may be operable to control a degree of freedom of the tool 840, and the sensor 828 may be operable to sense a position and/or state of the degree of freedom. For example, the actuator may be operable to control a joint of the tool 840, and the sensor may be operable to sense a position of the joint. In some embodiments, the tool may include a number of actuators and/or sensors for controlling a number of degrees of freedom of the tool 840. In at least one embodiment, the same electrical/optical contact 846 in each tool 840, that is, the contact that couples to contact 837 may be operable to control different degrees of freedom in different tools. For example, in one embodiment, contacts 837 and 846 may be operable to control a roll of a first tool, whereas contacts 837 and 846 may be operable to control a pitch of a second tool.

Further, the connector 834 of the manipulator arm 820 may also include an electrical/optical contact 837 for electrically/optically engaging the contact 846 of the tool 840 so as to facilitate communication between the tool 840 and the manipulator arm 820. Similar to actuators 826 and sensors 828 of the manipulator arm 820, the contact 837 may be coupled to one or more contacts 832 of the connector 830 at the proximal end of the manipulator arm 820 such that information can be communicated between the tool 840 and the support structure 850.

Figure 8C:
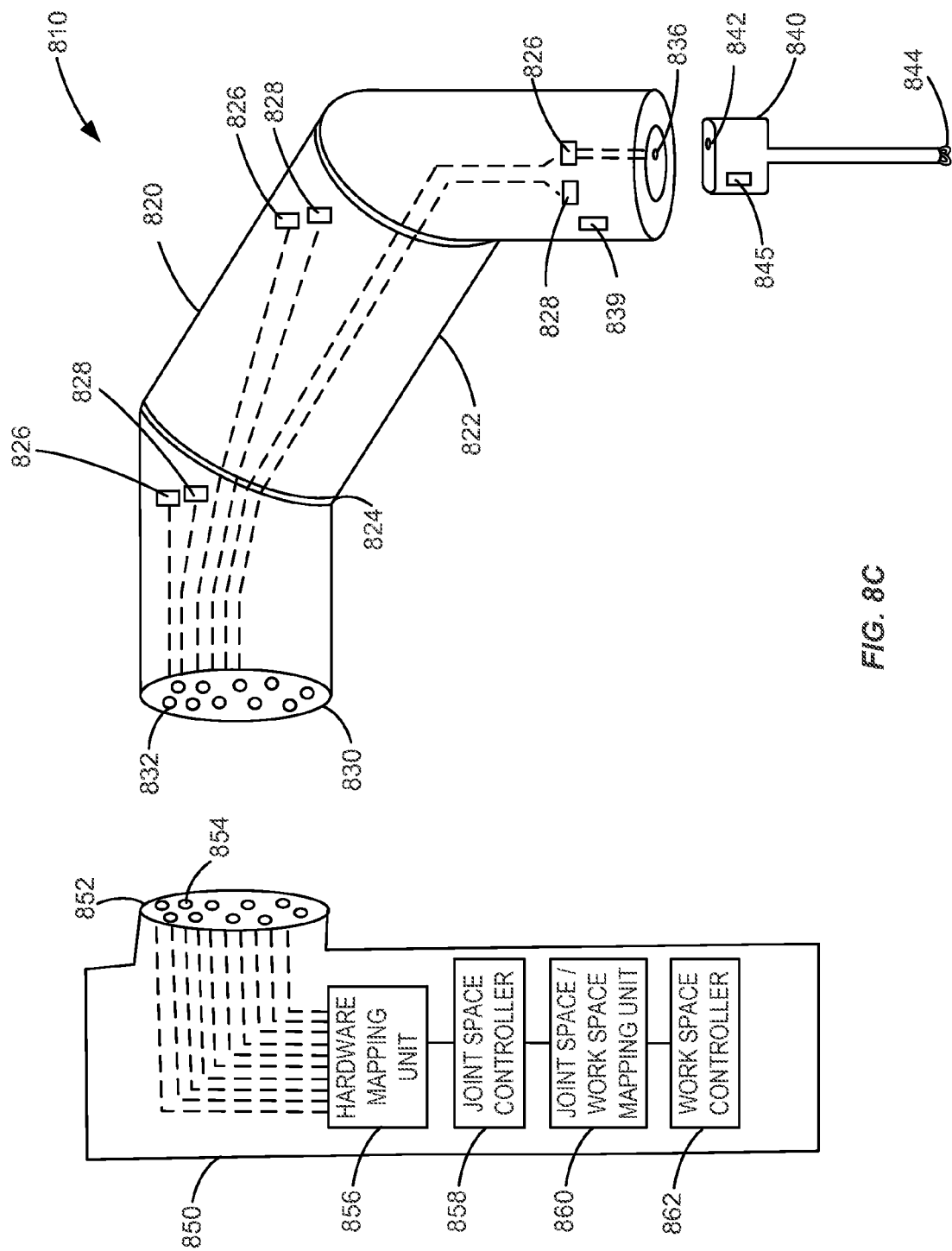
FIG. 8C is part of a robotic system including a manipulator assembly and a support structure according to a third embodiment.

FIG. 8C is part of a robotic system including a manipulator assembly 810 and a support structure 850 according to a third embodiment. The manipulator assembly 810 and support structure 850 in this embodiment are similar to that discussed with reference to FIG. 8A, and thus the structures and functions discussed with reference to FIG. 8A are equally applicable for this embodiment.

The tool 840 in this embodiment includes a tool identification unit 845. The tool identification unit 845 may store a tool identifier that identifies one or more characteristics of the tool. For example, the tool identifier may identify the type of tool (e.g., endoscope, jaws, vacuum, electrosurgical paddle, etc.), the number of degrees of freedom of the tool (e.g., 3 degrees of freedom, 4 degrees of freedom, 5 degrees of freedom, etc.), the types of degrees of freedom (e.g., motion degrees of freedom such as roll, translate, etc., actuation degrees of freedom such as activating a vacuum or electrode, etc.), etc. The tool identification unit 845 may be operable to communicate the tool identifier to other elements of the robotic system, such as elements of the support structure. The tool identifier may then be used for a variety of purposes, such as for configuring the hardware mapping unit 845 and/or the joint space work space mapping unit 860.

The tool identification unit 845 may be implemented using one or more of a variety of techniques. For example, the tool identification unit 845 may be coupled to a contact (e.g., contact 846) of the tool 840 and may thus be operable to communicate the tool identifier via one or more wires. For another example, the tool identification unit 845 may be operable to wirelessly communicate the tool identifier. For example, the tool identification unit 845 may be a radio frequency identification (RFID) chip having an identifier associated with one or more characteristics of the tool 840. Accordingly, the manipulator arm 820 may include an RFID reader 839 for reading the tool identifier when the tool 840 is within range of the manipulator arm 820. The RFID reader 839 may be coupled to one or more contacts 832 of the connector 830 such that the RFID reader 839 may be operable to communicate the tool identifier to other elements of the robotic system such as elements of the support structure 850.

In other embodiments, other wireless techniques may be used to communicate a tool identifier from the tool 840 to other elements of the robotic system. For example, the tool 840 and other elements of the robotic system (e.g., manipulator 820, support structure 850, or other elements) may include Bluetooth™ circuitry, wireless communication circuitry for communicating in accordance with IEEE 802.11 standards, the IrDA standard, or other wireless communication standards.

Further, in some embodiments, the manipulator arm 820 may also or alternatively include manipulator identification unit (not shown) that may store a manipulator identifier that identifies one or more characteristics of the manipulator and/or a connected tool. For example, the manipulator identifier may identify the type of manipulator (e.g., parallelogram), the number of degrees of freedom of the manipulator and/or a connected tool (e.g., 3 degrees of freedom, 4 degrees of freedom, 5 degrees of freedom, etc.), the types of degrees of freedom of the manipulator and/or a connected tool (e.g., motion degrees of freedom such as roll, translate, etc., actuation degrees of freedom such as activating a vacuum or electrode, etc.), etc. The manipulator identification unit may be operable to communicate the manipulator identifier to other elements of the robotic system, such as elements of the support structure. The manipulator identifier may then be used for a variety of purposes, such as for configuring the hardware mapping unit 845 and/or the joint space work space mapping unit 860. Like the tool identification unit 845, the manipulator identification unit may be operable to communicate the manipulator identifier to other elements of the robotic system via wired means (e.g., through a contact 832) or wireless means (e.g., via an RFID tag coupled to the manipulator arm 820 and an RFID reader coupled to the support structure 850).

Manipulator assembly 810 and support structure 850 in certain embodiments include various components such actuators, sensors, joints, tools, connectors, mapping units, and controllers. However, it will be appreciated by those of ordinary skill in the art that the input device could operate equally well by having fewer or a greater number of components than are illustrated in FIGS. 8A to 8C. It will be further appreciated by those of ordinary skill in the art that the elements described with reference to each of FIGS. 8A to 8C could be used simultaneously or separately from one another. For example, the identification systems described with reference to FIG. 8C could be used with the system described with reference to FIG. 8B. Thus, the depiction of the manipulator assembly 810 and support structure 850 in FIGS. 8A to 8C should be taken as being illustrative in nature, and not limiting to the scope of the disclosure.

Figure 9A:
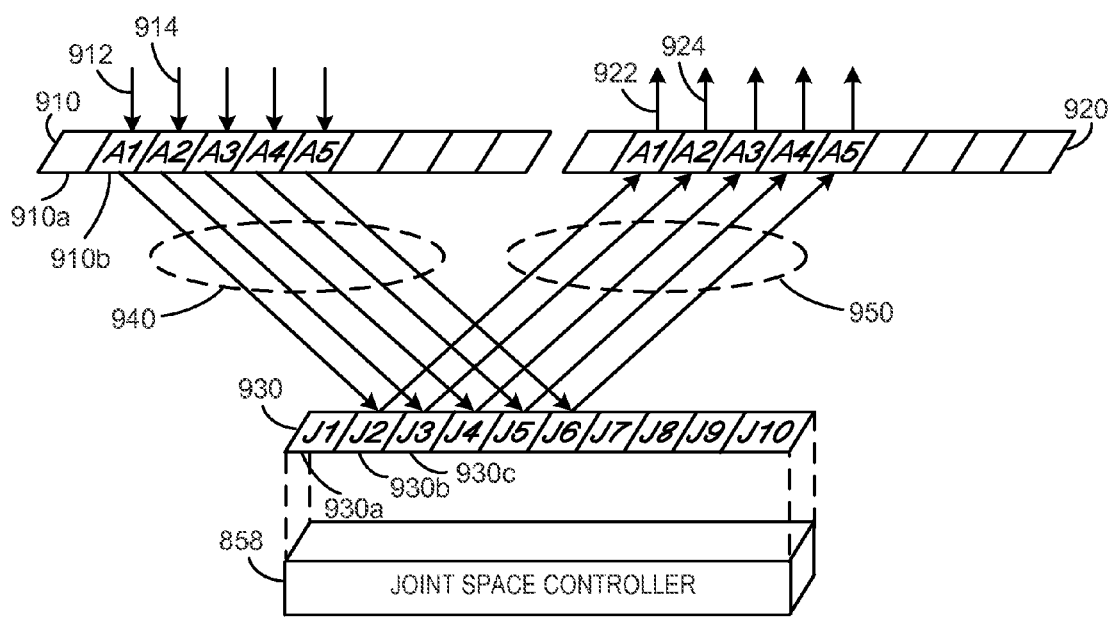
FIG. 9A illustrates a mapping between connector input/output elements and joint space interface elements according to a first embodiment.

FIG. 9A illustrates a mapping between connector input/output elements and joint space interface elements according to a first embodiment. The mapping as shown is illustrated as a first mapping between connector input elements 910, connector output elements 920, and joint space interface elements 930.

The connector input elements 910 are, in some embodiments, part of a layer of hardware devices, such as elements for receiving sensor signals of a manipulator assembly. For example, connector input elements 910 may correspond to electrical and/or optical contacts (e.g., contacts 854) designated to receive information from devices such as sensory devices located in a manipulator assembly (e.g., sensors 828). Accordingly, each contact may be operable to receive information from elements of the manipulator assembly.

In one embodiment, one or more of the connector input elements 910 receives a sensor signal 912. The sensor signal 912 may indicate the joint state of a connected manipulator assembly. For example, the sensor signal 912 may be information received from a sensor 828 that measures a position or state of a degree of freedom of the manipulator assembly 810. The degree of freedom may correspond to a degree of freedom of the manipulator arm 820 or, in some embodiments, to a degree of freedom of a connected tool 840.

In the example illustrated in FIG. 9A, the sensor signal 912 indicates the state or position of an outer yaw (A1) of the manipulator arm. Other sensor signals, such as sensor signal 914, may indicate the state or position of different joints of the connected manipulator assembly. For example, the sensor signal 914 in this example indicates the state or position of an outer pitch (A2) of the manipulator arm. Yet other sensor signals may indicate the state or position of even more joints of the connected manipulator assembly, such as an outer roll (A3), an insertion joint (A4), and an instrument roll (A5). It should be recognized that particular joint being indicated by the sensor signal received at the connector input elements 910 is, in many embodiments, determined by the manipulator assembly 810. That is, the sensor signal received at the connector input elements 910 may correspond to sensor signals provided at corresponding contacts (e.g., electrical and/or optical contacts 832) on the attached manipulator assembly, where the sensor signals provided at the contacts of the manipulator assembly may indicate different joints or degrees of freedom for different manipulator arms and/or tools. In some embodiments, the different joints or degrees of freedom of a manipulator assembly may result from changing a tool of the manipulator assembly.

The sensor signals provided at the connector input elements 910 are then communicated to the joint space interface elements 930 via a first mapping 940. The first mapping 940 may be generated by, for example, the hardware mapping unit 856, and may operate to map the received sensor signals to particular joint space interface elements 930.

The joint space interface elements 930 may include one or more elements having fixed or otherwise predefined characteristics. For example, the joint space interface elements 930 may be defined to each correspond to a particular degree of freedom of one or more manipulator assemblies (i.e., manipulator arms and/or tools). In the example illustrated in FIG. 9A, the joint space interface elements 930 are predefined to correspond to, e.g., a secondary outer yaw (J1), an outer yaw (J2), an outer pitch (J3), outer roll (J4), an insertion joint (J5), an instrument roll (J6), and additional joints (J7) to (J10).

In some embodiments, the joint space interface elements 930 may operate as input/output elements of an algorithm being executed by a processor or, in some embodiments into a controller such as joint space controller 858. Accordingly, the joint space controller 858 may be operable to process the sensor signals in joint space by, for example, executing one or more algorithms that loop over individual joints.

The joint space controller 858 may then be operable to output the results via the same or different joint space interface elements 930. In the example illustrated in FIG. 9A, the joint space controller 858 outputs the results using the same joint space interface elements 930. The output signals may be, for example, control signals for controlling one or more elements of the manipulator assembly such as actuators 826. The joint space interface elements 930 may be mapped to one or more connector output elements 920 via a second mapping 950. The second mapping 950 may be generated by, for example, the hardware mapping unit 856, and may operate to map the outputs of the joint space interface elements 930 to the connector output elements 920.

The connector output elements 920 are, in some embodiments, part of a layer of hardware devices, such as elements for sending control signals to a manipulator assembly. For example, connector output elements 920 may correspond to electrical and/or optical contacts (e.g., contacts 854) designated to send information to devices such as actuators located in a manipulator assembly (e.g., actuators 826). Accordingly, each contact may be operable to communicate information to elements of the manipulator assembly. In the example shown in FIG. 9A, a control signal 922 is output to an actuator of the manipulator assembly 810 for controlling an outer yaw of the manipulator assembly 810, whereas a control signal 924 is output to an actuator of the manipulator assembly 810 for controlling an outer pitch of the manipulator assembly 810.

In some embodiments, the connector input elements 910 and connector output elements 920 are separate from one another, whereas in other embodiments the connector input elements 910 and connector output elements 920 may be the same as one another. In the example shown in FIG. 9A, the connector output elements 920 are different than the connector input elements 910, indicating that some contacts 832 may be used for receiving sensor signals from sensors 828 whereas other contacts 832 may be used for sending control signals to actuators 826. However, in other embodiments, the connector output elements 920 may be the same as connector input elements 910, indicating that some contacts 832 may be used for both receiving sensor signals from sensors 828 and sending control signals to actuators 826.

Returning to the first mapping 940 and the second mapping 950, it should be apparent that these mappings operate to map signals received/communicated to the connector input/output elements to and from the appropriate joint space interface elements. In many embodiments, these mappings are different for different manipulator assemblies. For example, in the embodiment illustrated in FIG. 9A, the first connector input element 910a does not receive any signals from the manipulator assembly, whereas the second connector input element 910b may receive a sensor signal indicating a position or state of an outer yaw of the manipulator assembly. The first mapping 940 is then customized to that particular manipulator assembly, and operates to map the second connector input element 910b to the second joint space (e.g., joint space interface elements 930) interface element 930b, which the joint space controller 858 assumes and processes as an outer yaw degree of freedom. The first mapping 940 does not map any signal to the first joint space interface element 930a, since the manipulator assembly does not have any degree of freedom corresponding to a secondary outer yaw joint.

Figure 9B:
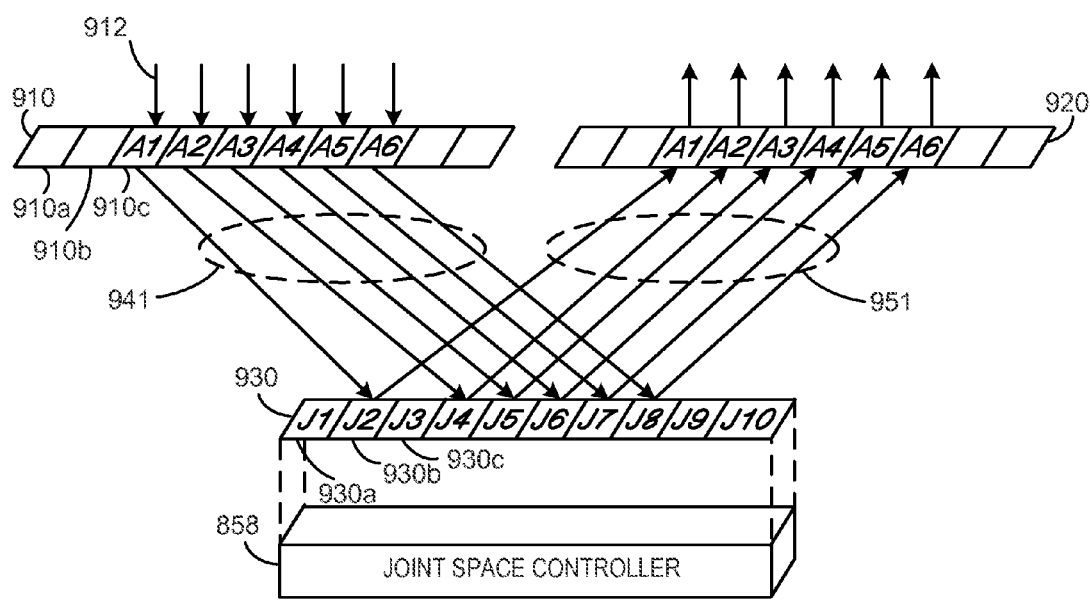
FIG. 9B illustrates a mapping between connector input/output elements and joint space interface elements according to a second embodiment.

Turning briefly to FIG. 9B, FIG. 9B illustrates a mapping between connector input/output elements and joint space interface elements according to a second embodiment. This embodiment is similar to that discussed with reference to FIG. 9A, except in this case the support structure 850 is coupled to a different manipulator assembly 820 (the manipulator assembly may be different as a result of changing a tool of the assembly) such that the sensor signal 912 is not received at the second connector input element 910b but rather is received at the third connector input element 910c. Since the joint space interface elements 930 do not change with different manipulator assemblies, the first mapping 940 must change so that the sensor signals received at the connector input elements 910 are mapped to the appropriate joint space interface elements 930. In the example of FIG. 9B, the first mapping 941 that corresponds to the new manipulator assembly maps the third connector input element 910c to second joint space interface element 930b, rather than to the third joint space interface element 930c as it did in the example of FIG. 9A. Similarly, the example in FIG. 9B may use a different second mapping 951 than that used in the example in FIG. 9A. By using different mappings for different manipulator assemblies, advantageously the same joint space controller 858 may be used for different manipulator assemblies.

Figure 9C:
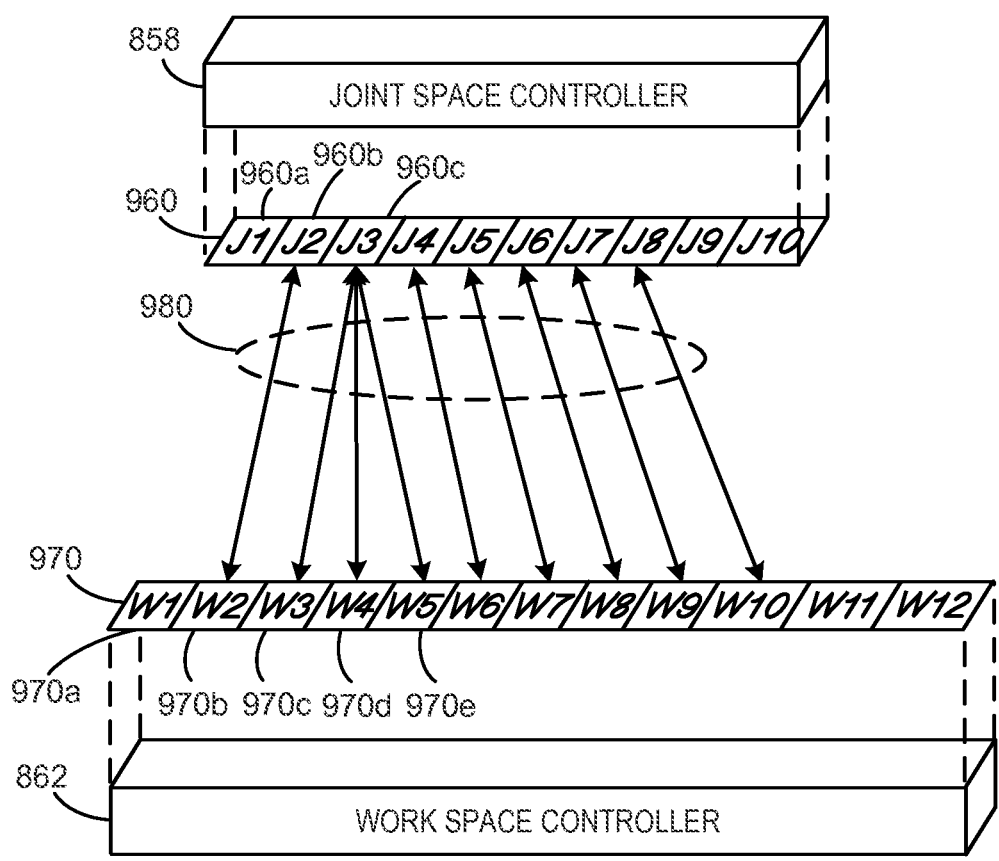
FIG. 9C illustrates a mapping between joint space interface elements and work space interface elements according to an embodiment.

FIG. 9C illustrates a mapping between joint space interface elements and work space interface elements according to an embodiment. The joint space interface elements 960 in this embodiment are mapped to work space interface elements 970 via a joint space work space mapping 980. The joint space interface elements 960 may be similar to those discussed with reference to FIGS. 9A and 9B, but in this embodiment may be operable to communicate information between the joint space controller 858 and the work space controller 862.

In some embodiments, the work space interface elements 970 may operate as input/output elements of an algorithm being executed by a processor or, in some embodiments, into a controller such as work space controller 862. Accordingly, the work space controller 862 may be operable to process signals output by the joint space controller 858 in a work space by receiving those signals via the work space interface elements 970. In at least one embodiment, the work space controller 862 corresponds to a layer of work space degrees of freedom or mechanical linkages. For example, each of the work space interface elements 970 may correspond to a particular linkage of a manipulator assembly. The work space controller 862 may be operable to perform calculations on outputs from the joint space controller 858 in one or more coordinate systems, such as a Cartesian coordinate system, a polar coordinate system, etc., in any suitable number of dimensions (e.g., one dimension, two dimensions, three dimensions, greater than three dimensions, etc.). The calculations performed by the work space controller may include, for example, forward kinematics, inverse kinematics, and other cart-space and null-space algorithms.

The joint space work space mapping 980 may be different for different manipulator assemblies, similar to the mappings discussed with reference to FIGS. 9A and 9B. The joint space work space mapping 980 operates to map joint space interface elements 960 to work space interface elements 970. For example, the joint space work space mapping 980 may map output signals from the joint space controller 858 to the appropriate work space interface elements 970, and similarly map output signals from the work space interface elements 970 to the appropriate joint space interface elements 960. In some embodiments, the joint space work space mapping 980 may be generated by, for example, the joint space work space mapping unit 860.

In some embodiments, a joint space interface element may not be mapped at all to a work space interface element, resulting in a fixed frame transformation. For example, the first joint space interface element 960a is not mapped to any work space interface elements 970, and the first work space interface element 970a is not mapped to any joint space interface elements 960. This may be the case where the attached manipulator assembly does not have a degree of freedom corresponding to the degree of freedom of the first joint space interface element 960a (e.g., a secondary outer yaw joint).

In at least one embodiment, a single joint space interface element may be mapped to a single work space interface element. For example, the second joint space interface element 960b may be mapped to the second work space interface element 970b. This may be the case where the attached manipulator assembly has a degree of freedom corresponding to the degree of freedom of the second joint space interface element 960b (e.g., an outer yaw degree of freedom), and that degree of freedom corresponds to movement of a single link.

In at least one embodiment, a single joint space interface element may be mapped to a number of work space interface elements. For example, the third joint space interface element 960c may be mapped to the third work space interface element 970c, the fourth work space interface element 970d, and the fifth work space interface element 970e. This may be the case where a portion of the manipulator is a parallel mechanism. A parallel mechanism is where multiple physical joints move simultaneously based on a single independent degree of freedom. One of the physical joints may be independently controlled, whereas motion of the other physical joints is dependent on movement of the independently controlled joint. Examples of parallel mechanisms include snake tools (which move a tool tip around a curve instead of pivoting along a single axis), a parallelogram axis, etc.

Figure 10:
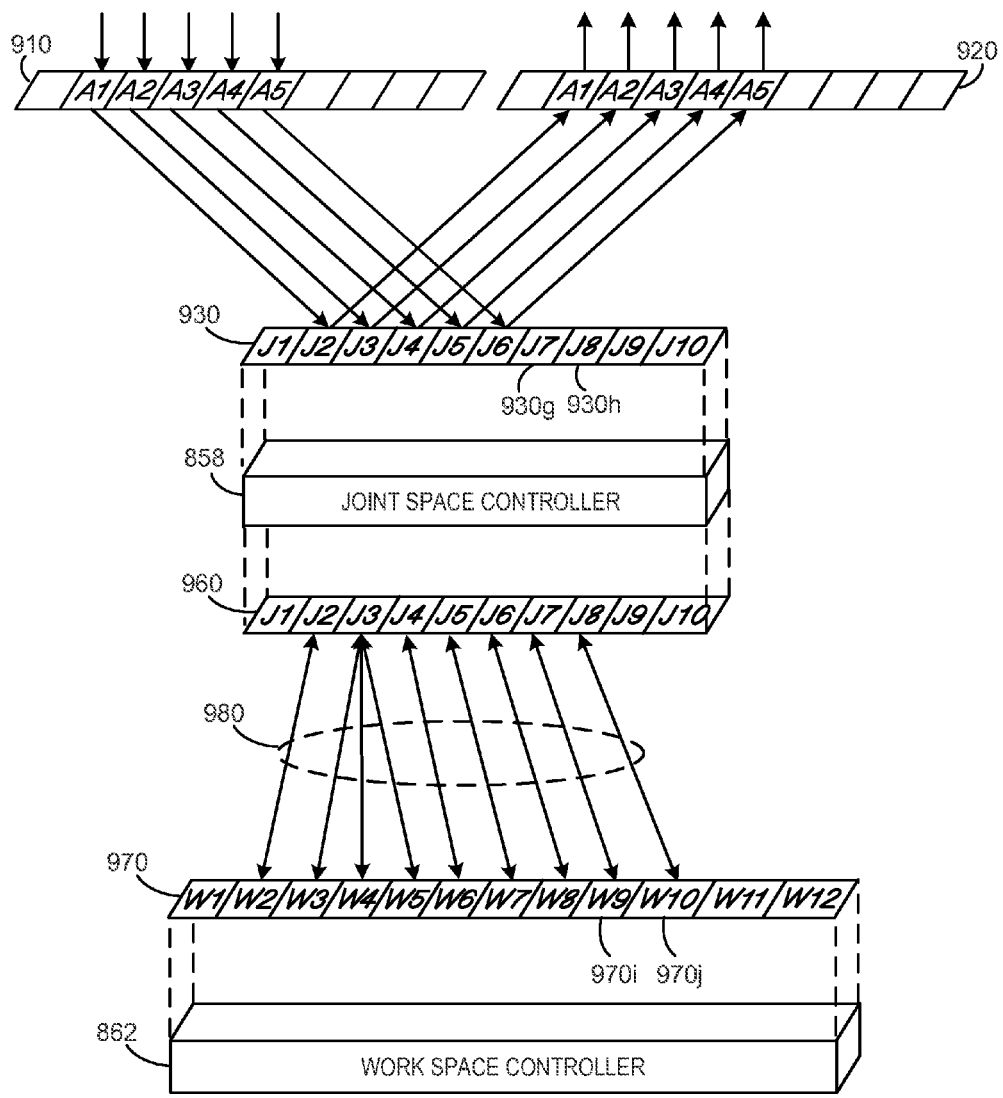
FIG. 10 illustrates mappings between connector input/output elements, joint space interface elements, and work space interface elements according to an embodiment.

FIG. 10 illustrates mappings between connector input/output elements, joint space interface elements, and work space interface elements according to an embodiment. The various devices, interface elements, signals, and mappings are similar to those discussed with reference to FIGS. 9A and 9C, but in this case are shown as a single interconnected system for mapping signals communicated to and from a manipulator assembly to signals eventually processed by a work space controller.

In at least one embodiment, in addition to processing actual signals received and communicated for controlling degrees of freedom of a manipulator assembly, the system may also be operable to perform processing for simulated or phantom degrees of freedom. For example, in some embodiments, a manipulator assembly may be missing one or more degrees of freedom, e.g., it may not be operable to roll. However, the calculations executed by controllers, such as the joint space controller 858 and/or work space controller 862, may be executed on the assumption that such degree(s) of freedom actually exist on the manipulator assembly.

For example, the joint space controller 858, although it does not receive input signals at the joint space interface elements 930g and 930h, which may correspond to degrees of freedom such as a particular roll and a pitch of the manipulator assembly, nor does the joint space controller 858 provide outputs at the joint space interface elements 930g and 930h, the joint space controller 858 may nonetheless execute algorithms on the presumption that the degrees of freedom corresponding to the joint space interface elements 930g and 930h are being controlled.

Accordingly, in some embodiments, the joint space work space mapping 980 may include a mapping for processing signals associated with these phantom degrees of freedom. For example, the joint space work space mapping 980 may map the joint space interface element 930g corresponding to, e.g., a phantom pitch, to a work space interface element 970i, and may map the joint space interface element 930h corresponding to, e.g., a phantom yaw, to a work space interface element 970j. The work space controller 862 may then also perform calculations, similar to the joint space controller 858, on the presumption that the links corresponding to the work space interface elements 970i and 970j exist and are being controlled, although in reality they are not being controlled and may not even exist on the connected manipulator assembly.

The number of connector input elements 910, connector output elements 920, joint space interface elements 930, and work space interface elements 970 may be any suitable number for controlling a plurality of manipulator assemblies. In one embodiment, the number of joint space interface elements is greater than the number of connector (input and/or output) elements. Such an arrangement may advantageously allow for a number of different manipulator assemblies having a number of different degrees of freedom that may be controlled to all be controlled by the same joint space controller. In cases where the number of joint space interface elements is greater than the number of connector elements, the connector elements may be mapped to a subset of the joint space interface elements. Further, in cases where different manipulator assemblies have the same number of degrees of freedom, but at least one different degree of freedom (e.g., one manipulator includes an outer pitch degree of freedom, whereas another manipulator does not include an outer pitch degree of freedom but includes an additional tool degree of freedom), the connector elements for each of the manipulators may be mapped to different subsets of the joint space interface elements. In other embodiments, the number of connector elements used by different manipulator assemblies may also be different.

In some embodiments, the number of work space interface elements is greater than the number of joint space interface elements. Such an arrangement may advantageously allow for one joint space interface element to be mapped to more than one cart space interface element, thereby facilitating control of a variety of mechanical linkages for a given manipulator assembly degree of freedom.

Figure 11A:
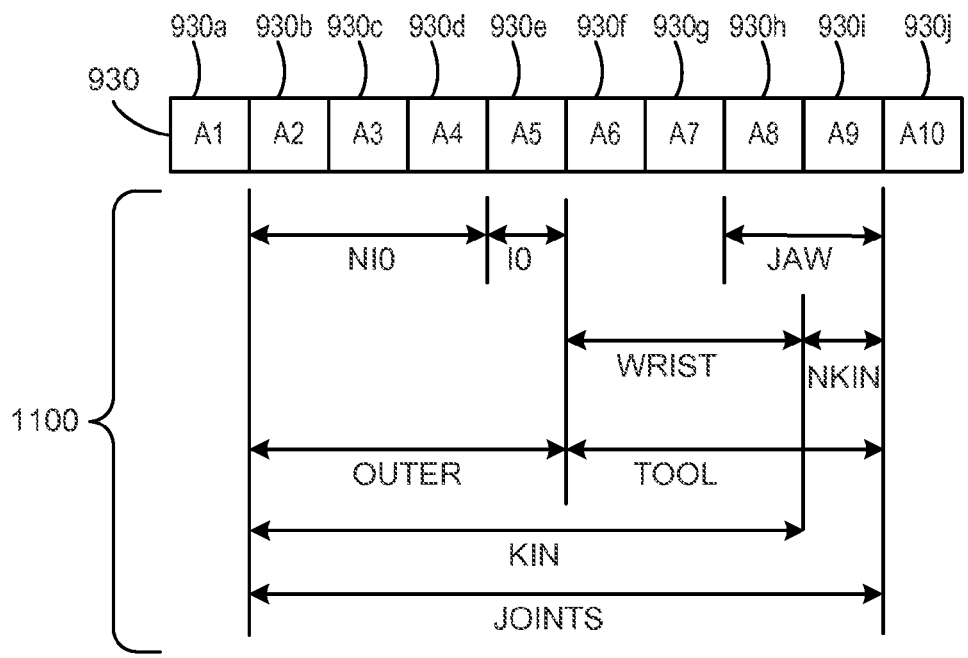
FIG. 11A shows a first set of groupings of the degrees of freedom of a first manipulator assembly being controlled by the joint space interface elements.
Figure 11B:
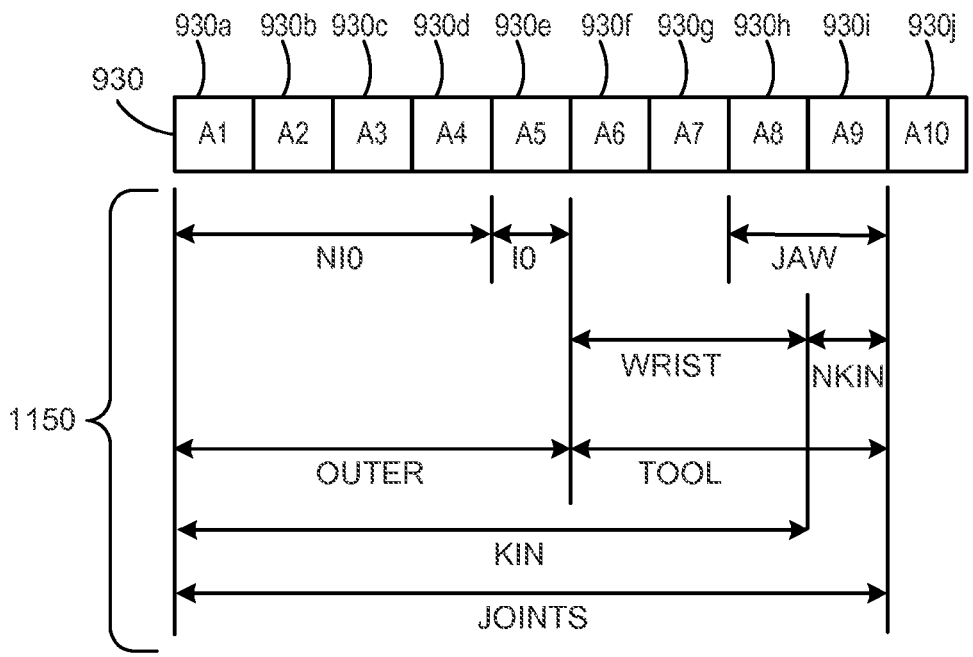
FIG. 11B shows a second set of groupings of the degrees of freedom of a second manipulator assembly being controlled by the joint space interface elements.

Turning briefly to FIGS. 11A and 11B, FIG. 11A shows a first set of groupings 1100 of the degrees of freedom of a first manipulator assembly being controlled by the joint space interface elements 930, and FIG. 11B shows a second set of groupings 1150 of the degrees of freedom of a second manipulator assembly being controlled by the joint space interface elements 930. Here, the second manipulator assembly is different than the first manipulator assembly, and thus the groupings may also be different.

In some embodiments, algorithms executed by, e.g., the joint space controller, may operate on only a subset of available inputs. For example, algorithms executed by the joint space controller 858 may operate on (e.g., acquire input from, process, and send outputs to) only a subset of interface elements 930. The different algorithms, while receiving and operating on different sets of inputs, may be executed simultaneously with one another. In situations where different manipulators (and, in some embodiments, different tools) are sequentially connected to the same connector of a support structure (i.e., one manipulator is swapped out for another manipulator), the joints of the manipulator being controlled by the interface elements 930 may change. As a result, the specific interface elements 930 which algorithms operate on may similarly change.

To account for these changes, different joint groupings may be used, where a joint group definition defines a particular joint grouping. For example, with reference to FIGS. 11A and 11B, which each illustrate a particular interface grouping, interface elements 930b through 930e may correspond to outer joints of a first manipulator (FIG. 11A), whereas interface elements 930a through 930e may correspond to outer joints of a second manipulator (FIG. 11B). When one or more algorithms are structured to operate only on outer joints of a manipulator, when the first manipulator (FIG. 11A) is connected the algorithm(s) may read the joint groupings definition for that manipulator and determine that the outer joints are fully defined using interface elements 930b through 930e. Thus, the algorithm(s) may operate only on those interface elements. For example, a first algorithm may operate using the "outer" group of interface elements 930b through 930e, and a second algorithm may (simultaneously or sequentially) operate using the "tool" group of interface elements 930f through 930i. In contrast, when the second manipulator (FIG. 11B) is connected the algorithm may read the joint groupings definition for that manipulator and determine that the outer joints are fully defined using interface elements 930a through 930e. Thus, the algorithm(s) may operate on those interface elements (i.e., inclusive of interface element 930a). For example, a third algorithm may operate using the "outer" group of interface elements 930a through 930e, and a fourth algorithm may operate using the "tool" group of interface elements 930f through 930i. Each of the first, second, third and fourth algorithms may be different from one another and optimized to execute on the particular group of interface elements. For example, one algorithm may be optimized to execute on a group of input elements associated with outer joints of a manipulator assembly, whereas another algorithm may be optimized to execute on a group of input elements associated with degrees of freedom of a tool.

A joint groupings definition may define all of the joint groupings used by the algorithms in the controller for a particular manipulator. For example, with reference to FIG. 11A, the joint groupings definition may define the groupings for "joints", "tool", "jaw", etc., for a first manipulator as depicted in FIG. 11A. With reference to FIG. 11B, a different joint groupings definition may define (in some cases, different) groupings for "joints", "tool", "jaw", etc., for a second manipulator as depicted in FIG. 11B. The joint groupings definitions for different manipulators may be stored at the controllers (e.g., in support structure 850), or may be acquired from a suitable source (e.g., from the manipulator, from a remote storage device, etc.) when or before a manipulator is connected for use.

In the particular embodiments depicted in FIGS. 11A and 11B, at least some of the groupings illustrated in FIG. 11A are the same as those illustrated in FIG. 11B since the manipulator assembly being controlled by the interface elements of FIG. 11A has at least some of the same degrees of freedom as those of the manipulator assembly being controlled by the interface elements of FIG. 11B. For example, both sets of groupings group the eighth joint space interface element 930h and the ninth joint space interface element 930i into a "jaw" grouping indicating the joint space interface elements that operate to control a jaw of a tool. Further, both sets of groupings group the sixth joint space interface element 930f, seventh joint space interface element 930g, and eighth joint space interface element 930h, into a "wrist" grouping indicating the joint space interface elements that operate to a control a wrist of the tool.

Further, at least some of the groupings illustrated in FIG. 11A are different than those illustrated in FIG. 11B since the manipulator assembly being controlled by the interface elements of FIG. 11A does not include a secondary outer yaw joint, whereas the manipulator assembly being controlled by the interface elements of FIG. 11B does include a secondary outer yaw joint. Accordingly, a grouping defined as "outer", which identifies the joint space interface elements that operate to control the manipulator arm, is defined for the first set of groupings 1100 to include the second, third, fourth, and fifth joint space interface elements 930b to 930e. In contrast, the grouping defined as "outer" is defined for the second set of groupings 1100 to include the first, second, third, fourth, and fifth joint space interface elements 930a to 930e, as the secondary outer yaw joint corresponds to a degree of freedom of the manipulator arm rather than a connected tool.

As mentioned, algorithms executed by the joint space controller may select the signals to use from the joint space interface elements 930 based on input data received for the algorithm(s). For example, input data from a sensor, actuator, and/or work space controller may indicate to the algorithm(s) which joint space interface elements correspond to, e.g., tool degrees of freedom, and thus the joint space controller may use signals received from (and communicate processed signals to) the appropriate joint space interface elements. In other embodiments, the signals may be selected based on a predetermined correspondence between the joint space interface elements and degrees of freedom of the manipulator assembly. For example, upon connecting a particular manipulator assembly, grouping information indicating the groupings of different joint space interface elements may be loaded that corresponds to the particular manipulator assembly. Thus, the joint space controller may use signals received from (and communicate processed signals to) the appropriate joint space interface elements defined by the particular grouping.

Figures 12A, 12B:
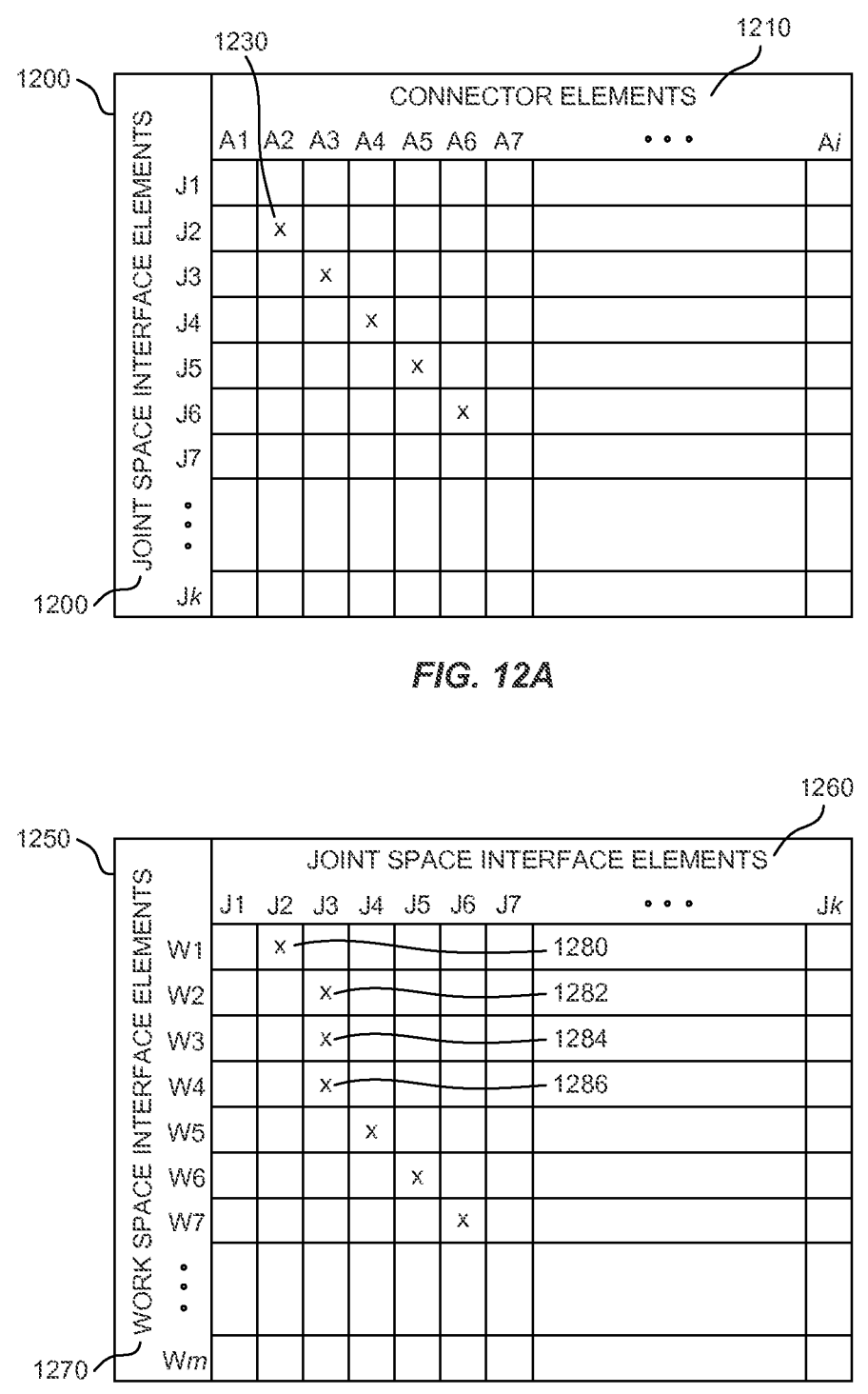

Turning now to FIGS. 12A and 12B, FIG. 12A shows a connector/joint space map 1200 according to an embodiment, while FIG. 12B shows a joint space/work space map 1250 according to an embodiment. The maps may be stored in any suitable element of the robotic system, such as a storage element in the support structure 850. The connector/joint space map 1200 is a map for mapping (e.g., first mapping 940 and/or second mapping 950) connector elements 1210 (e.g., contacts 854) to joint space interface elements 1220 (e.g., joint space interface elements 930). The connector/joint space map 1200 may include any suitable number of connector elements, such as A1 to Ai (where i is any integer), and any suitable number of joint space interface elements, such as J1 to Jk (here k is any integer). A mapping indicator 1230 may indicate a particular mapping between a particular connector element and a particular joint space interface element. For example, with reference to FIG. 9A, connector element "A2" may correspond to second connector input element 910b, and the joint space interface element "J2" may correspond to the second joint space interface element 960b. Accordingly, the mapping indicator 1230 may be operable to map a signal between the second connector input element 910b and the second joint space interface element 960b.

The joint space/work space map 1250 is a map for mapping (e.g., joint space work space mapping 980) joint space interface elements 1260 (e.g., joint space interface elements 930) to work space interface elements 1220 (e.g., work space interface elements 970). The joint space/work space map 1250 may include any suitable number of joint space elements, such as J1 to Jk (where k is any integer), and any suitable number of work space interface elements, such as W1 to Wm (where m is any integer). A mapping indicator 1280 may indicate a particular mapping between a particular joint space element and a particular work space interface element. For example, with reference to FIG. 9C, joint space interface element "J2" may correspond to the second joint space interface element 960b, and the work space interface element "W1" may correspond to the second work space interface element 970b. Accordingly, the mapping indicator 1280 may be operable to map a signal between the second joint space interface element 960b and the second work space interface element 970b.

Further, the maps may be operable to map one element to more than one element. For example, again with reference to FIG. 9C, joint space interface element "J3" may correspond to the third joint space interface element 960c, and the work space interface elements "W2", "W3", and "W4" may respectively correspond to the second, third, and fourth work space interface elements 970c to 970e. First, second, and third mapping indicators 1282, 1284, and 1286 may thus be operable to map a signal between the third joint space interface element 960*c* and each of the second, third, and fourth work space interface elements 970*c* to 970*e*.

The support structure in certain embodiments includes various interface elements and controllers such as connector elements, interface elements, mappings, joint space controllers, work space controllers, etc. However, it will be appreciated by those of ordinary skill in the art that the input device could operate equally well by having fewer or a greater number of components than are illustrated in FIGS. 9A to 12B. It will be further appreciated by those of ordinary skill in the art that the elements described with reference to each of FIGS. 9A to 12B need not require the particular mappings nor the particular degrees of freedom illustrated and discussed with reference to these embodiments. For example, some of the degrees of freedom may correspond to movement of a connected manipulator arm, whereas other degrees of freedom may correspond to movement of a connected tool, whereas yet other degrees of freedom may correspond to actuation of a tool or manipulator arm. Thus, the depiction of the various elements in FIGS. 9A to 12B should be taken as being illustrative in nature, and not limiting to the scope of the disclosure.

Figure 13A:
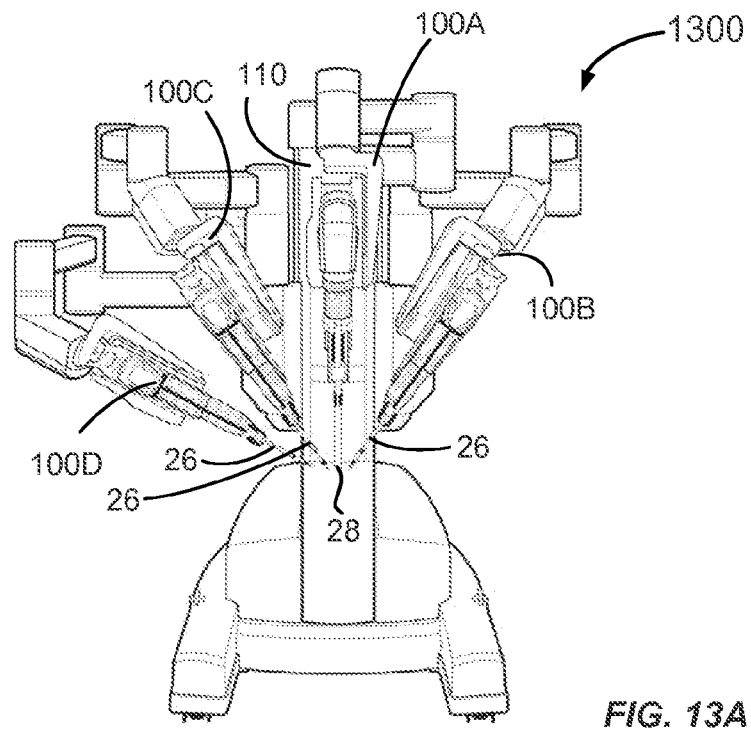
FIG. 13A shows a patient side cart including an imaging device coupled to a first manipulator arm and a surgical tool coupled to a second manipulator arm.

FIG. 13A shows a patient side cart 1300 similar to patient side cart 22 depicted in and discussed with reference to FIG. 4. However, in this embodiment, the manipulator arms are individually identified and include a first manipulator arm 100A, a second manipulator arm 100B, a third manipulator arm 100C, and a fourth manipulator arm 100D. The first manipulator arm 100A is coupled to an imaging device 28, whereas the second, third and fourth manipulator arms (100B, 100C, 100D) are each coupled to a respective surgical tool 26.

Figure 13B:
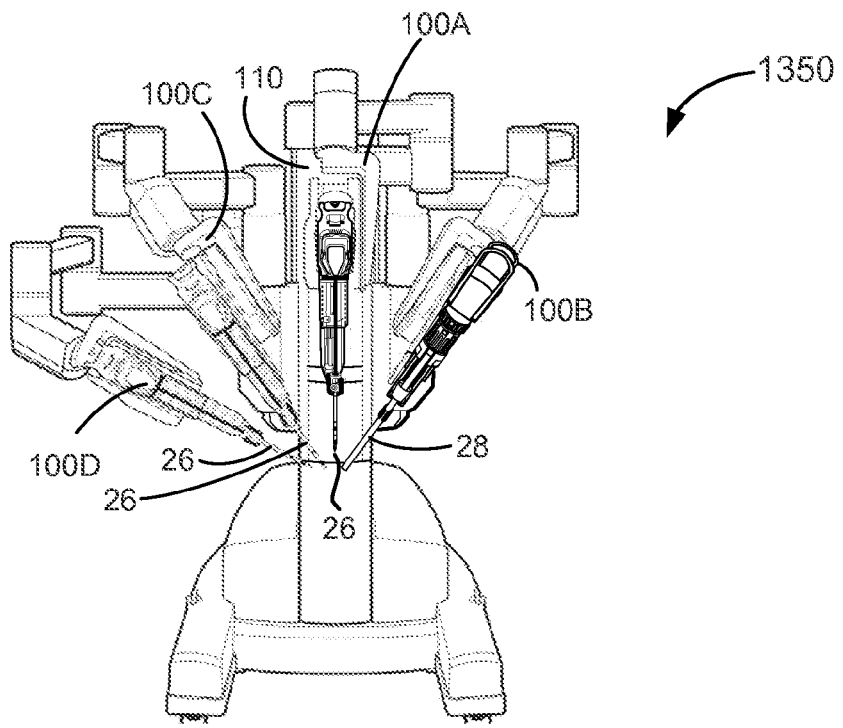
FIG. 13B shows a patient side cart including an imaging device coupled to the second manipulator arm and a surgical tool coupled to the first manipulator arm.

FIG. 13B shows a patient side cart 1350 similar to patient side cart 1300. However, in this embodiment, the first manipulator arm 100A is coupled to a surgical tool 26 whereas the second manipulator arm 100B is coupled to the imaging device 28. That is, the imaging device has been swapped with one of the surgical tools.

In many embodiments, the imaging device 28 can be swapped with a surgical tool 26 at any suitable time, including during a medical procedure on a patient without turning off or otherwise rebooting the software executing on the patient side cart 1350 or other elements of the MIRS system 10 (FIG. 1). Swapping the imaging device 28 with a surgical tool 26 may facilitate changes in the field of view of the imaging device 28, and may facilitate changes in the accessible work space available to the swapped out surgical tool.

In at least one embodiment, a frame of reference of the surgical tooltip is changed as a result of moving the imaging device 28 (e.g., a camera) from one manipulator to another manipulator. For example, when performing surgery it is generally desirable to rearrange things in space so that the frame of reference of a surgical tooltip relative to the camera tip matches the frame of reference of an input device used by a surgeon to control the surgical tool relative to an image display viewed by the surgeon. When a surgical tool is coupled to a first manipulator arm, and an imaging device is coupled to a second manipulator arm, the surgeon (via, e.g., an input device) is driving the surgical tool via the first manipulator. The surgical tool tip frame relative to the imaging device frame is thus used for tele-operation. However, the surgical tool and imaging device are swapped with one another, the surgeon ends up driving the imaging device. As a result, the system (e.g., one or more algorithms executed by the joint space controller and/or the work space controller) defines an arbitrary frame of reference (i.e., a world frame) such that the imaging device frame relative to the world frame is used for tele-operation.

One skilled in the art would recognize that various techniques disclosed herein can be used to assist in facilitating the swapping of image devices and surgical tools. For example, the first manipulator arm 100A and the second manipulator arm 100B may each be similar to manipulator 820 (FIGS. 8A to 8C), and each of the imaging device 28 and surgical tool 26 may be similar to the tool 840. Accordingly, each of the first manipulator arm 100A and the second manipulator arm 100B may include a connector (e.g., connector 834) that is shaped to engage a corresponding connector of the imaging device 28 and the surgical tool 26.

Various processing that may be performed by, e.g., support structure 850 to facilitate the hot-swapping of imaging devices and surgical tools is further described with reference to FIGS. 14 to 16B. One skilled in the art would recognize that embodiments are not limited to swapping imaging devices with surgical tools, but include swapping surgical tools with other surgical tools, imaging devices with other types of imaging devices, etc.

Figure 14:
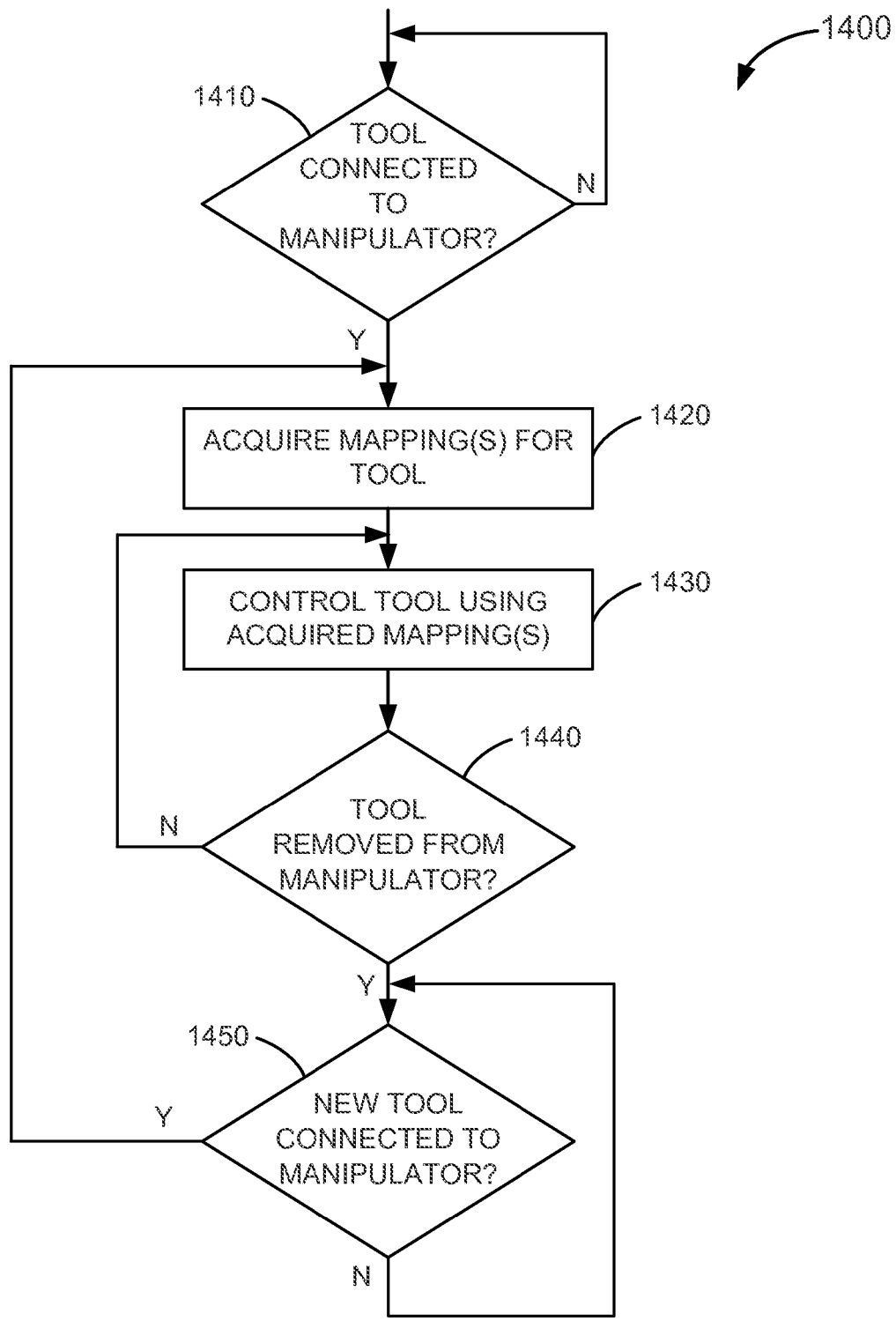
FIG. 14 shows a sequence of operations that may be used to control one from a number of possible tools connected to the same manipulator arm.

FIG. 14 shows a sequence of operations that may be used to control one from a number of possible tools connected to the same manipulator arm. Or, more generally, to control a number of different manipulator assemblies, where a manipulator assembly includes both a manipulator arm and a tool. The operations may be performed by any suitable controller, such as any of those described herein with reference to support structure 850 (FIG. 8A to 8C).

In operation 1410, it is determined whether a tool is connected to a manipulator. For example, joint space controller 858 (or a different controller) may determine whether tool 840 is connected to manipulator arm 820. When it is determined that a tool is not connected to the manipulator arm, the system may continue to monitor the manipulator arm to determine whether a tool is connected. Otherwise, processing may continue to operation 1420.

In operation 1420, a mapping for the connected tool is acquired. The mapping may include one or more mappings, such as those described with reference to FIGS. 8A through 12B. For example, the mappings may include a connector/joint space map 1200 (FIG. 12A), a joint space/work space map 1250 (FIG. 12B), or any other suitable map that associated with the connected tool. The mappings may be acquired using any one or more of a number of techniques, some of which are described with reference to FIG. 15.

Once mappings for the tool are acquired, processing continues to operation 1430. In operation 1430, the connected tool is controlled using the acquired mapping. For example, the tool may be controlled using the joint space controller 858 and the work space controller 862 using the connector/joint space map and the a joint space/work space map. Various techniques for using one or more maps to control a tool are described with reference to FIGS. 8A through 12B. Any one or more of those techniques are applicable for controlling the connected tool. Further techniques for controlling the connected tool are described with reference to FIGS. 16A and 16B.

In operation 1440 it is determined whether the tool is removed from the manipulator. For example, a controller determines whether the tool 840 is removed from the manipulator arm 820. If it is determined that a tool is not removed from the manipulator arm, then tool may continue to be controlled using the acquired mappings. Otherwise, processing continues to operation 1450.

In operation 1450, it is determined whether a new tool is connected to the manipulator. This operation is similar to operation 1410. If it is determined that a new tool is connected, then a mapping for the new tool may be acquired in operation 1420, and the new tool may then be controlled using the new mapping in operation 1430. Otherwise, the system may continue to monitor for connection of a new tool.

As a result of the mappings, the same software kernel can be used by processors (e.g., the joint space controller 858 and/or the work space controller 862) that control the different tools connected to the same manipulator arm. The software kernel may include the functionality of all different types of tools that can be connected to the manipulator arm, such as acquiring images from an imaging device, actuating forceps, etc. The software kernel then has the capability to actuate any function of all of the tools, while the tool mappings provide the appropriate signal routing such that different tools having different degrees of freedom can effectively be controlled when connected to the same manipulator arm.

Figure 14A:
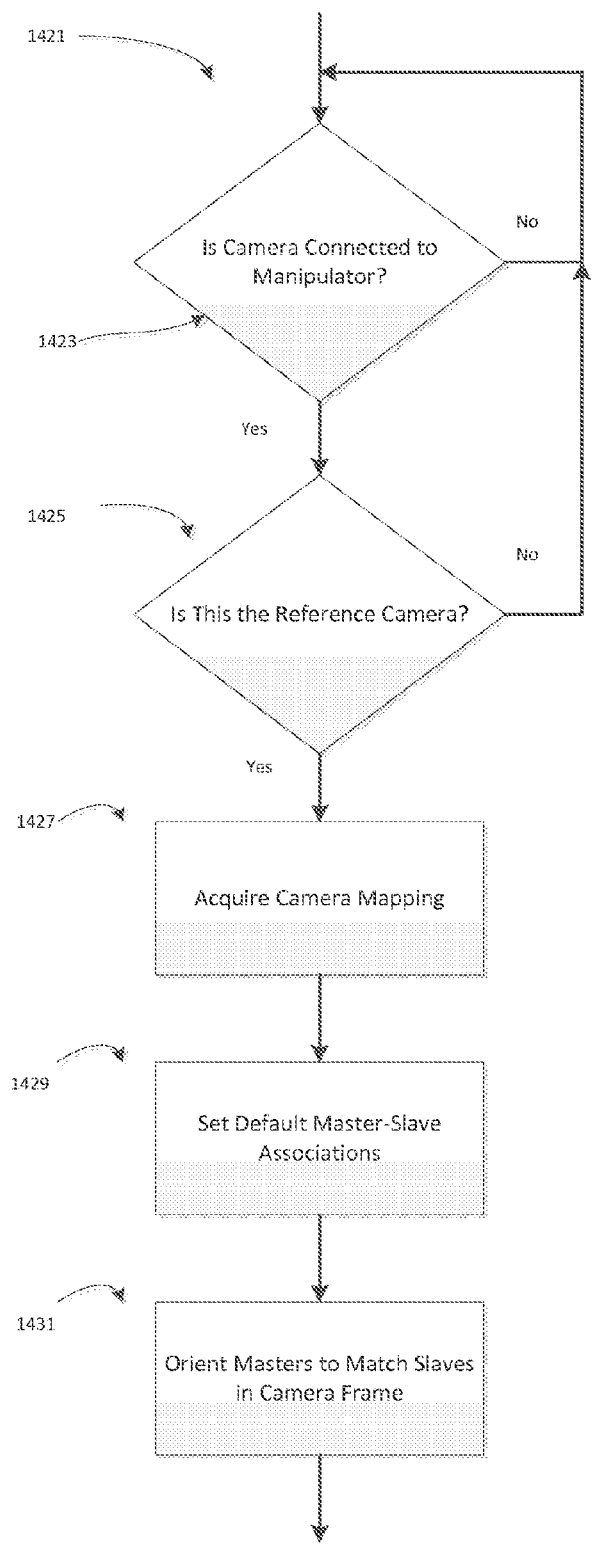
FIG. 14A shows a sequence of operations that may be used when an imaging device is removed from a first manipulator arm and coupled to a second manipulator arm so as to maintain correspondence between movement of surgical tools imaged by the image capture device as displayed to a system user and input devices being manipulated by the system user.

Referring now to FIG. 14A, an example of a sequence of operations 1421 for acquiring mappings for one or a tool may be used when, for example, a tool mounted to a manipulator of the patient side cart may be an image capture device or a surgical instrument, so as to facilitate changes to a frame of reference when appropriate. This exemplary sequence of operations may be included within operation 1420 of FIG. 14 when acquiring mapping, and may help maintain correlation between movement commands input by a system user (such as by moving a handle of an input device) and corresponding movement of a tip of a surgical instrument as imaged by an image capture device (including an image capture device newly mounted to a manipulator) and as displayed to the system user. Additional details regarding the correlation between the input and display of the moving instrument can be understood, for example, with reference to U.S. Pat. No. 6,424,885, entitled "Camera Referenced Control in a Minimally Invasive Surgical Apparatus," the full disclosure of which is incorporated herein by reference.

In operation 1423, it is determined whether a camera or other image capture device has been connected to a manipulator. The mounting of a camera to a manipulator may be determined by signals transmitted between the camera and the manipulator, or by an input from a system user. In operation 1425, it is determined that the camera or other image capture device that has been mounted to the manipulator is the reference camera. Where only one camera is to be mounted to the manipulator system and/or where the camera that has been mounted is the first camera to be mounted to the manipulator system the system may, in response, designate the camera that has been mounted as the reference camera. Optionally, the designation of the reference camera may be in response to an input by a system user, a type of camera, or the like. If no camera has been mounted or the mounted camera is not the reference camera the system may continue to monitor for mounting of the reference camera.

Figure 14B:
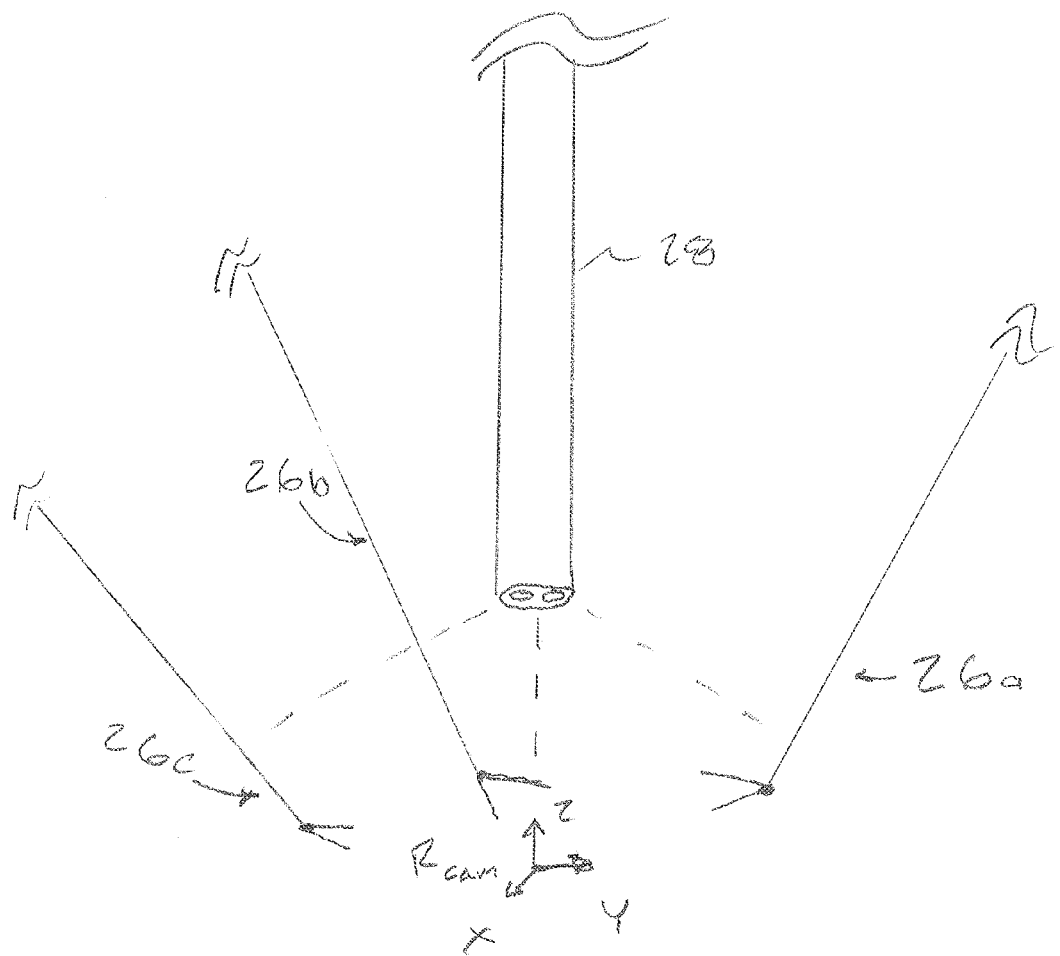
FIGS. 14B and 14C show tool tips before and after a tool swap, respectively, and schematically indicate associated changes to a camera reference coordinate system for controlling surgical instruments.
Figure 14C:
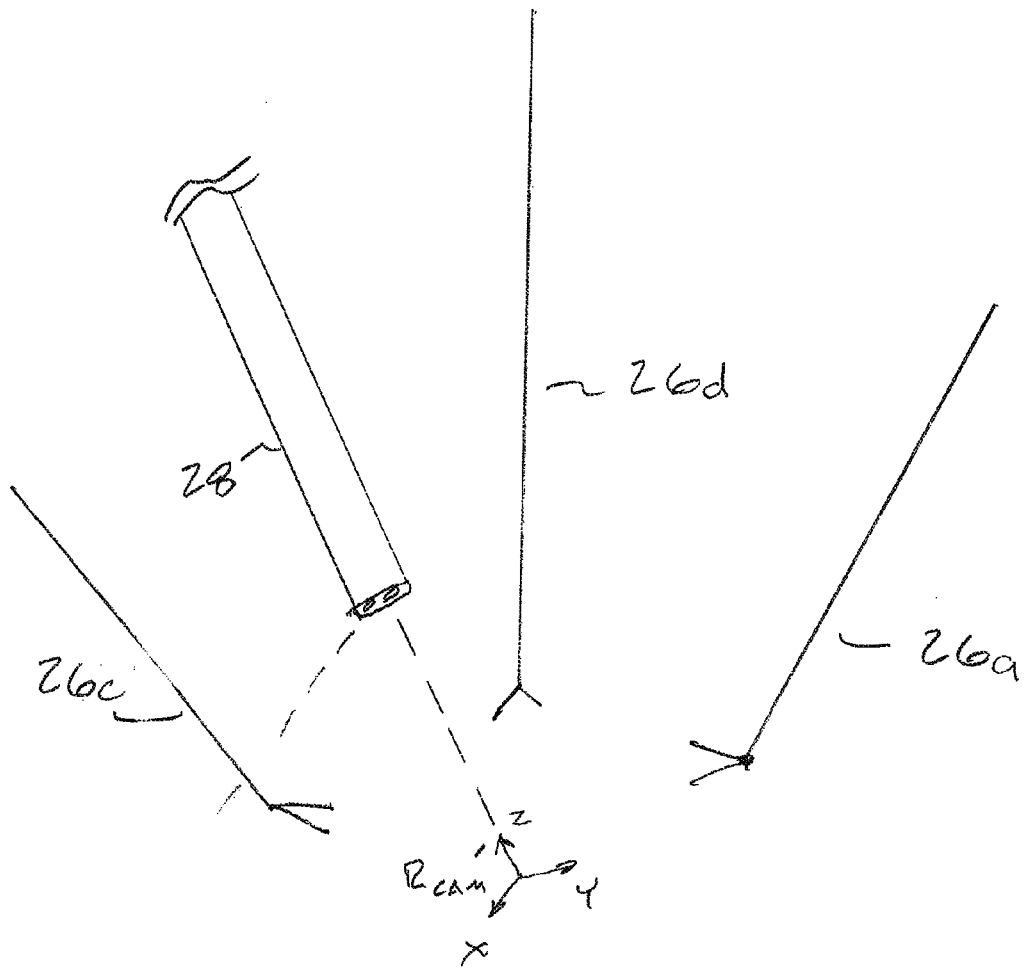

In operation 1427, when a reference camera has been mounted to the manipulator system the system acquires a mapping of a camera mapping. For example, referring to FIG. 14B before a camera swap operation a camera 28 may have a camera reference coordinate frame of reference $R_{cam}$ that can be identified (optionally relative to a world coordinate reference system) by the system controller using signals from the potentiometers or other joint state sensors associated with each of the joints of the robotic arm (including the first manipulator 100A as shown in FIG. 13A) and set-up joints or other structures supporting the camera), together with known attributes of the robotic arms (such as the kinematics of the system associated with the joint state sensors). Similar mappings of each of the tool tips in the field of view of the camera of surgical instruments 26a, 26b, 26c and their associated manipulators 100B, 100C, 100D to $R_{cam}$ can be used by the controller to help maintain correlation between movement command vectors and the resulting tool tip motions. Referring to FIG. 14C, after a tool swap operation, camera 28 may be mounted to manipulator 100B or another of the manipulators. Operation 1427 acquires a new mapping of the newly mounted camera 28 using the joint state signals of manipulator 100B to derive a new camera reference frame $R_{cam}'$. The new camera reference frame may then be used to determine joint commands for movement of the camera and/or for movement of all the surgical instruments mounted to the other manipulators, including surgical instrument 26d mounted to manipulator 100A (which previously supported camera 28). Note that instrument 26d may optionally be the same instrument 26b which was removed from manipulator 100B prior to the tool swap, or may be a different instrument. Similarly, camera 28 may be the same camera that was supported by manipulator 100A prior to the tool swap or may be a different camera.

In operation 1429, default master-slave associations between input devices and surgical instruments may be set. The associates may be determined, for example, in response to relative positions of the input devices relative to the user display and tool tips of the surgical instruments relative to the camera reference frame. Hence, right and left input devices are associated with surgical instruments which appear in the display to be to the right and left side of the workspace, respectively. Note that the user may manually set associates when desired, and that when the arrangement of tools is not amenable to automated or default associations (such as in the arrangement of FIG. 13B where left and right tools are somewhat arbitrary) the system may prompt and/or wait for user input on appropriate master-slave associations. Master-Slave associates in more complex systems having multiple concurrent users may allow user control over those associates as described in more detail in U.S. Pat. No. 8,666,544 entitled "Cooperative Minimally Invasive Telesurgical System," the disclosure of which is also incorporated herein by reference.

In operation 1431, the master input devices may be moved (in orientation and/or position) to match the associated slave tool tips. Movement of the masters may be performed by actuating motors of the masters as described, for example, in U.S. Pat. No. 6,364,888 entitled "Alignment of Master and Slave in a Minimally Invasive Surgical Apparatus," the full disclosure of which is incorporated herein by reference. Once the masters have been moved the system may be ready to initiate telepresence following, or for another desired operations in preparation for following.

Figure 15:
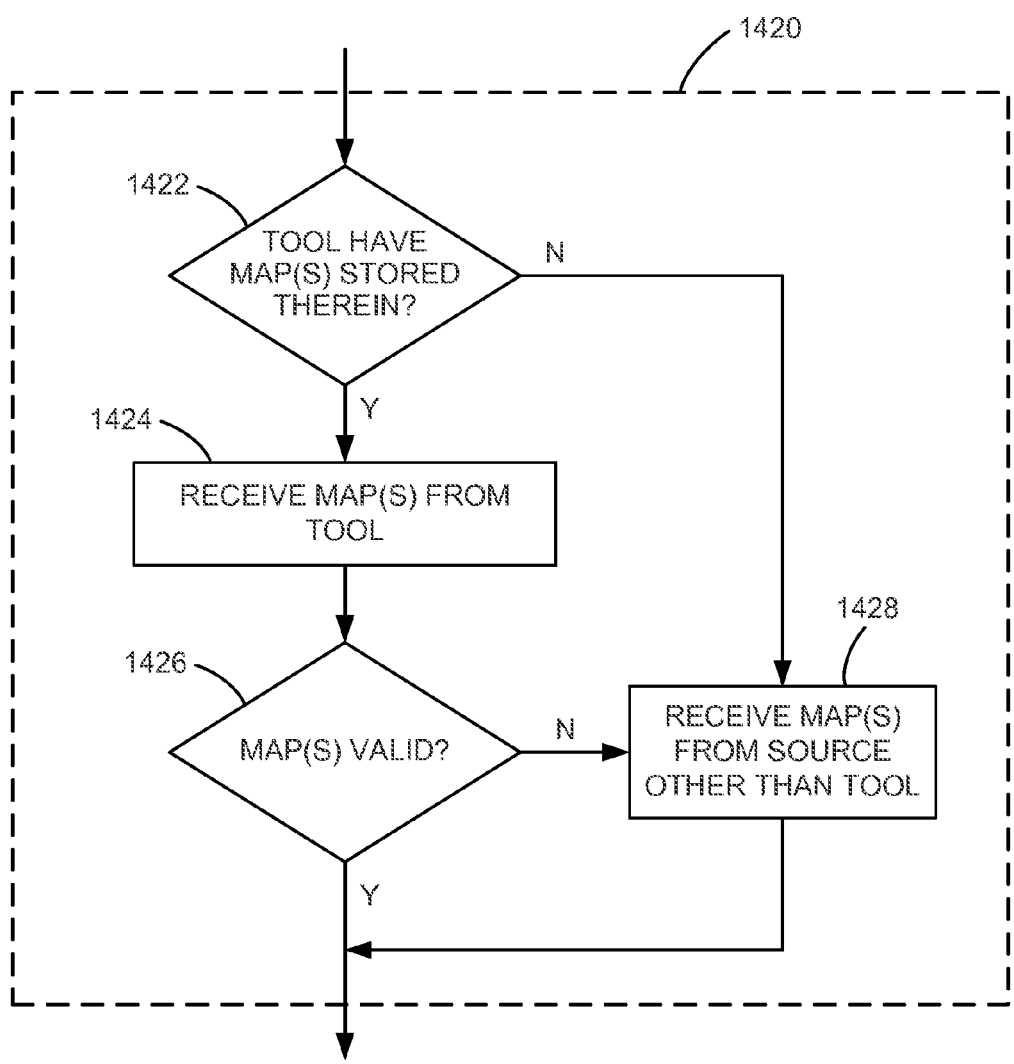
FIG. 15 shows a sequence of operations for acquiring mappings for a tool according to an embodiment.

Turning now to FIG. 15, FIG. 15 shows a sequence of operations for acquiring mappings for a tool according to an embodiment. In operation 1422, it is determined whether the tool has the mappings stored therein. For example, the mappings may be stored on a storage medium of the tool.

When it is determined that the tool does not have the mappings stored therein, then processing may continue to operation 1428. In operation 1428, the mappings are received from a source other than the tool. For example, the hardware mapping unit 856 and/or the joint space/work space mapping unit 860 may receive the mappings from a source other than the tool. The source may be any electronic device other than the tool that has mappings stored thereon.

For example, the source may be a remote server, a local hard drive, etc. The mappings received from such a source may then subsequently be used for controlling the tool.

When it is determined that the tool does have the mappings stored therein, then processing may continue to operation 1424. In operation 1424, the mappings are received from the tool. For example, the hardware mapping unit 856 and/or the joint space/work space mapping unit 860 may receive the mappings from storage element of the tool. This may be wired or wireless communication using any suitable communication protocol. Once the mappings are received from the tool, then processing may continue to operation 1426.

In operation 1426 it is determined whether the mappings received from the tool are valid. For example, a controller such as the hardware mapping unit 856, work space controller 862, or other suitable controller may determine whether the received mappings are valid. This may include determining whether the mappings are out of date, are corrupt, are for the wrong tool, etc. If it is determined that the mappings are invalid, then processing may continue to operation 1428 as previously described. Otherwise, the mappings received from the tool may subsequently be used to control the tool.

It should be recognized that techniques for acquiring the mappings for a tool are not limited to those described with reference to FIG. 15. Rather, embodiments also include other techniques for acquiring mappings. For example, the controllers may simply download and use mappings provided by the tool or a source other than the tool. For another example, the controllers may have locally stored mappings for each tool. One skilled in the art would recognize other variations, and such variations are intended to be covered within the scope of this application.

Figure 16A:
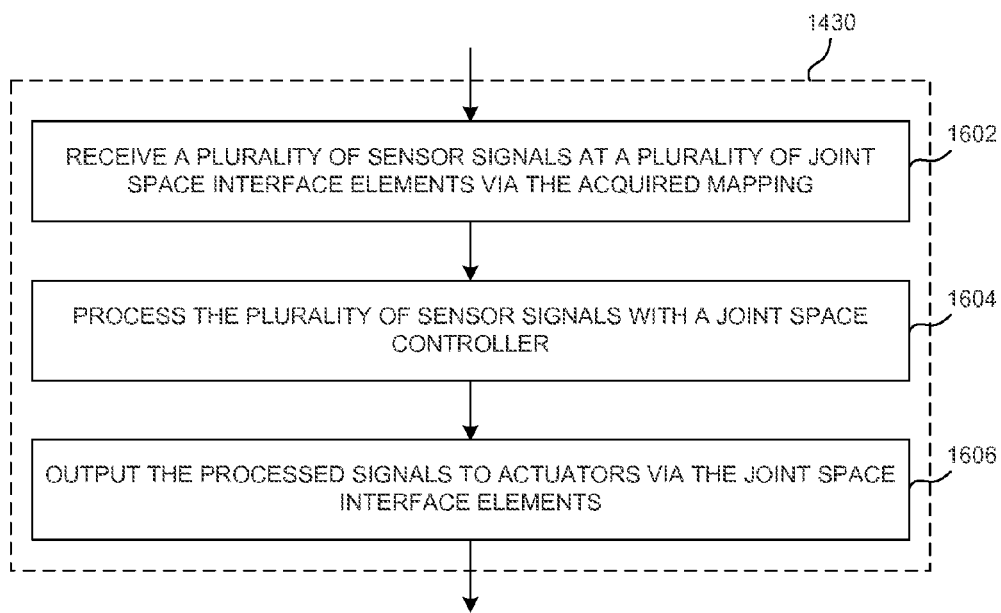
FIG. 16A shows a sequence of operations that may be used to control a tool using an acquired mapping in accordance with one embodiment.
Figure 16B:
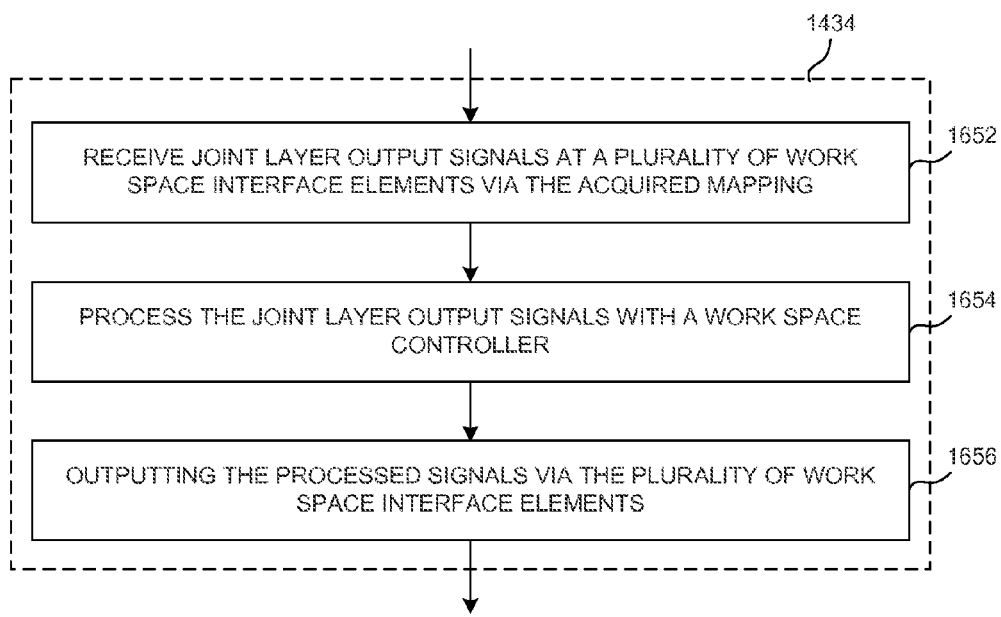
FIG. 16B shows a sequence of operations that may be used to control a tool using an acquired mapping in accordance with another embodiment.

Turning now to FIGS. 16A and 16B, FIG. 16A shows a sequence of operations 1430 that may be used to control a tool using an acquired mapping in accordance with one embodiment. In operation 1602, a plurality of sensor signals are received at a plurality of joint space interface elements. For example, with reference to FIG. 9A, sensor signals 912, 914, etc. may be received at joint space interface elements 930 from the connector input elements 910 via the first mapping 940.

In operation 1604, the received sensor signals may be processed with a joint space controller. For example, the sensor signals may be processed by joint space controller 858. In one embodiment, the joint space controller may execute algorithms on the received signals in joint space and then provide the output signals to control the connected manipulator assembly. In another embodiment, such as that discussed with reference to FIG. 16B, the joint space controller may execute algorithms on the received signals in joint space and then provide the output signals to another controller, such as a work space controller 862, for further processing.

In some embodiments, at least one additional signal may be processed in addition to the received sensor signals. For example, as discussed with reference to FIG. 10, the system may be operable to perform processing simulated or phantom degrees of freedom. Accordingly, the joint space controller 858 may be operable to process an additional signal such as a phantom input at the joint space interface element 930g and/or the joint space interface element 930h.

In operation 1606, the processed signals are output to actuators via the joint space interface elements. For example, the processed signals may be output from the joint space interface elements 930 and sent to the connector output elements 920 via the second mapping 950, where the processed signals operate to control one or more degrees of freedom of the connected manipulator assembly.

In embodiments where the manipulator assembly is changed (e.g., swapping of a manipulator arm and/or swapping of a tool), the same operations may subsequently be performed for the new manipulator assembly. For example, if an imaging device is first connected to a manipulator arm, a plurality of sensor signals may be received via an acquired mapping unique to that imaging device. If the imaging device is then swapped with a surgical tool, a new plurality of sensor signals are received at the same joint space interface elements via an acquired mapping unique to the surgical tool. In such a fashion, different manipulator assemblies can be controlled using a single software kernel.

Turning now to FIG. 16B, FIG. 16B shows a sequence of operations 1430 that may be used to control a tool using an acquired mapping in accordance with another embodiment. In one embodiment, these operations may be performed as operations in step 1430 of FIG. 14. In another embodiment, these operations may be performed as part of operation 1604 (FIG. 16A).

In operation 1652, joint layer output signals are received at a plurality of work space interface elements via the acquired mapping. For example, with reference to FIG. 9C, signals output from the joint space controller 858 may be received at work space interface elements 970 from the joint space interface elements 960 via the joint space work space mapping 980. Such joint layer output signals may correspond to those processed signals received from a first manipulator assembly, and thus may correspond to degrees of freedom of the first manipulator assembly.

In one embodiment, a single work space interface element (e.g., 970b) may receive an output signal from a single corresponding joint layer interface element (e.g., 960b), where in other embodiments, a number of work space interface elements (e.g., 970c, 970d, and 970e) may receive the same output signal from a single joint layer interface element (e.g., 960c). Further, in at least one embodiment, a work space interface element (e.g., 970i) may receive an output signal from a joint space interface element corresponding to a simulated degree of freedom of the manipulator assembly (e.g., 930g).

In operation 1654, the joint layer output signals are processed with a work space controller. For example, the output signals may be processed by work space controller 865. In one embodiment, the work space controller may execute algorithms on the received signals in the work space and then provide the output signals back to the joint space controller to control the connected manipulator assembly. In another embodiment, the work space controller may communicate the processed signals to other elements of the control system, such as the master input device.

In operation 1656, the processed signals are output to a plurality of joint space interface elements. For example, the processed signals may be output from the work space interface elements 970 to the joint space interface elements 960 via the joint space work space mapping 980, where the signals may be further processed by the joint space controller 858 and, in some embodiments, subsequently used to control the first manipulator assembly.

It should be appreciated that the specific operations illustrated in FIGS. 14 to 16B provide particular methods of controlling manipulator assemblies according to certain embodiments of the present invention. Other sequences of operations may also be performed according to alternative embodiments. For example, alternative embodiments of the present invention may perform the operations outlined above in a different order. Moreover, the individual operations illustrated in FIGS. 14 to 16B may include multiple sub-operations that may be performed in various sequences as appropriate to the individual operation. Furthermore, additional operations may be added or existing operations removed depending on the particular applications. One of ordinary skill in the art would recognize and appreciate many variations, modifications, and alternatives.

Further, it should be recognized that while the terms tools, instruments, surgical tools, surgical instruments and the like are often used interchangeably, in some embodiments they may not have identical meanings. For example, surgical instruments and surgical tools may refer to instruments or tools that are used for actively manipulating a patient, such as forceps, clamps, cutters, suction tubes, needles, drills, etc. In contrast, non-surgical instruments or tools may refer to those that are not used for actively manipulating a patient, such as an imaging device. The general term of tools or instruments may broadly cover both surgical and non-surgical instruments or tools.

The operations described in this application may be implemented as software code to be executed by one or more processors using any suitable computer language such as, for example, Java, C++ or Perl using, for example, conventional or object-oriented techniques. The software code may be stored as a series of instructions, or commands on a computer-readable medium, such as a random access memory (RAM), a read-only memory (ROM), a magnetic medium such as a hard-drive or a floppy disk, or an optical medium such as a CD-ROM. Any such computer-readable medium may also reside on or within a single computational apparatus, and may be present on or within different computational apparatuses within a system or network.

The present invention can be implemented in the form of control logic in software or hardware or a combination of both. The control logic may be stored in an information storage medium as a plurality of instructions adapted to direct an information processing device to perform a set of steps disclosed in embodiments of the present invention. Based on the disclosure and teachings provided herein, a person of ordinary skill in the art will appreciate other ways and/or methods to implement the present invention.

The use of the terms "a" and "an" and "the" and similar referents in the context of describing embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope unless otherwise claimed. No language in the specification should be construed as indicating any non-claimed element as essential to the practice of at least one embodiment.

Preferred embodiments are described herein, including the best mode known to the inventors. Variations of those preferred embodiments may become apparent to those of ordinary skill in the art upon reading the foregoing description. The inventors expect skilled artisans to employ such variations as appropriate, and the inventors intend for embodiments to be constructed otherwise than as specifically described herein. Accordingly, suitable embodiments include all modifications and equivalents of the subject matter recited in the claims appended hereto as permitted by applicable law. Moreover, any combination of the above-described elements in all possible variations thereof is contemplated as being incorporated into some suitable embodiment unless otherwise indicated herein or otherwise clearly contradicted by context. The scope of the invention should, therefore, be determined not with reference to the above description, but instead should be determined with reference to the pending claims along with their full scope or equivalents.

What is claimed is:

1. A method for controlling a telesurgical system, the method comprising:
   controlling, by a controller of the telesurgical system, a first tool connected to a first manipulator of the telesurgical system, the first tool being connected to the first manipulator using a plurality of first connector elements;
   implementing, by a hardware mapping unit, a first mapping between the plurality of first connector elements and a plurality of interface elements of the controller, the first mapping being used by the controller to control the first tool while it is connected to the first manipulator;
   controlling, by the controller, a second tool connected to a second manipulator of the telesurgical system, the second tool being connected to the second manipulator using a plurality of second connector elements;
   implementing, by the hardware mapping unit, a second mapping between the plurality of second connector elements and the plurality of interface elements of the controller, the second mapping being used by the controller to control the second tool while it is connected to the second manipulator;
   detecting, by the controller, a swap of the first and second tools such that the first tool is connected to the second manipulator using the plurality of first connector elements and the second tool is connected to the first manipulator using the plurality of second connector elements;
   implementing, by the hardware mapping unit, a third mapping between the plurality of first connector elements and the plurality of interface elements of the controller, the third mapping being different from the first and second mappings;
   implementing, by the hardware mapping unit, a fourth mapping between the plurality of second connector elements and the plurality of interface elements of the controller, the fourth mapping being different from the first and second mappings;
   controlling, by the controller, the first tool connected to the second manipulator using the fourth mapping; and
   controlling, by the controller, the second tool connected to the first manipulator using the third mapping.

2. The method of claim 1, wherein the first tool is an imaging device and the second tool is a surgical instrument.

3. The method of claim 2, wherein a coordinate reference frame used for images received from the imaging device for display to a user changes from a first coordinate reference frame based on kinematics of the first manipulator to a second coordinate reference frame based on kinematics of the second manipulator upon swapping of the first and second tools.

4. The method of claim 2, wherein controlling the surgical instrument prior to detecting the swap includes driving a control frame of the surgical instrument relative to a control frame of the imaging device, and controlling the imaging device after detecting the swap includes driving a control frame of the imaging device relative to an arbitrary reference frame.

5. The method of claim 1, wherein the first, second, third, and fourth mappings route signals between the controller and the first and second tools.

6. The method of claim 1, wherein the controller is a joint space controller.

7. The method of claim 1, wherein the first tool and the second tool are controlled using a same software kernel.

8. A telesurgical system for performing minimally invasive surgery on a patient, comprising:
a plurality of robotic manipulators each operable to receive one of a plurality of tools including an imaging device and a surgical instrument; and
a controller operable to:
control an imaging device connected to a first manipulator of the robotic manipulators and a surgical instrument connected to a second manipulator of the robotic manipulators;
detect a swap of the imaging device and the surgical instrument such that the imaging device is connected to the second manipulator and the surgical instrument is connected to the first manipulator;
change, based on detection of the swap, a reference coordinate frame for images received from the imaging device from a first reference coordinate frame based on kinematics of the first manipulator to a second reference coordinate frame based on kinematics of the second manipulator; and
control the imaging device connected to the second manipulator and the surgical instrument connected to the first manipulator.

9. The telesurgical system of claim 8, further comprising: a surgeon's console including a display element, wherein the images are displayed on the display element based on the reference coordinate frame.

10. The telesurgical system of claim 8, wherein being operable to control the surgical instrument prior to detecting the swap includes being operable to drive a control frame of the surgical instrument relative to a control frame of the imaging device, and being operable to control the imaging device after detecting the swap includes being operable to drive a control frame of the imaging device relative to an arbitrary reference frame.

11. The telesurgical system of claim 8, further comprising a plurality of connector elements operable to communicate signals between the first manipulator and the imaging device or the surgical instrument.

12. The telesurgical system of claim 11, further comprising a hardware mapping unit operable to change a mapping between the plurality of connector elements and a plurality of interface elements coupled to the controller.

13. The telesurgical system of claim 12, wherein the mapping is changed from a first map defining relationships between the plurality of connector elements and the plurality of interface elements unique to the imaging device to a second map defining relationships between the plurality of connector elements and the plurality of interface elements unique to the surgical instrument.

14. The telesurgical system of claim 8, wherein the controller includes a kernel operable to control both the imaging device and the surgical instrument.

15. The telesurgical system of claim 8, wherein the first manipulator and the second manipulator each include a mechanical interface configured to mechanically connect each of the first manipulator and the second manipulator to both of the imaging device and the surgical instrument independently.

16. The telesurgical system of claim 15, wherein the first manipulator and the second manipulator each include an electrical interface configured to electrically connect each of the first manipulator and the second manipulator to both of the imaging device and the surgical instrument independently.

17. A method for controlling a telesurgical system, the method comprising:
determining, by a controller, whether a first tool is connected to a manipulator of the telesurgical system using a plurality of connector elements;
acquiring, by the controller, a first mapping for the first tool when it is determined that the first tool is connected to the manipulator, the first mapping including a mapping between the plurality of connector elements and a plurality of interface elements of the controller;
implementing, by a hardware mapping unit, the first mapping;
controlling, by the controller, the first tool using the first mapping;
determining, by the controller, whether the first tool is removed from the manipulator and a second tool is connected to the manipulator using the plurality of connector elements;
acquiring, by the controller, a second mapping for the second tool when it is determined that the first tool is removed from the manipulator and a new the second tool is connected to the manipulator;
implementing, by the hardware mapping unit, the second mapping; and
controlling, by the controller, the second tool using the second mapping.

18. The method of claim 17, wherein the first tool is an imaging device and the second tool is a surgical instrument.

19. The method of claim 17, wherein acquiring the first mapping for the first tool includes receiving the first mapping from the first tool.

20. The method of claim 17, wherein acquiring the first mapping for the first tool includes receiving the first mapping from a storage element external to the first tool.

21. The method of claim 17, wherein the first mapping routes signals between the controller and the first tool.

22. The method of claim 17, wherein the second mapping routes signals between the controller and the second tool.

* * * * *

UNITED STATES PATENT AND TRADEMARK OFFICE
CERTIFICATE OF CORRECTION

PATENT NO. : 9,504,527 B2
APPLICATION NO. : 14/218300
DATED : November 29, 2016
INVENTOR(S) : Niels Smaby et al.

Page 1 of 1

It is certified that error appears in the above-identified patent and that said Letters Patent is hereby corrected as shown below:

In the Claims

In Column 42, Line 44 (Claim 17, Line 21), after "manipulator and" and before "the second tool" remove "a new".

Signed and Sealed this
Eighteenth Day of September, 2018

Andrei Iancu
*Director of the United States Patent and Trademark Office*